US012453803B2

(12) United States Patent
Park

(10) Patent No.: US 12,453,803 B2
(45) Date of Patent: Oct. 28, 2025

(54) COMPOSITE POSITIVE AND NEGATIVE POISSON'S RATIO MATERIALS FOR MEDICAL DEVICES

(71) Applicant: Joon Bu Park, Las Vegas, NV (US)

(72) Inventor: Joon Bu Park, Las Vegas, NV (US)

( * ) Notice: Subject to any disclaimer, the term of this patent is extended or adjusted under 35 U.S.C. 154(b) by 0 days.

(21) Appl. No.: 17/404,434

(22) Filed: Aug. 17, 2021

(65) Prior Publication Data

US 2023/0058045 A1 Feb. 23, 2023

(51) Int. Cl.

| | |
|---|---|
| ***A61L 31/14*** | (2006.01) |
| ***A61F 2/915*** | (2013.01) |
| ***A61L 31/02*** | (2006.01) |
| *A61F 2/00* | (2006.01) |

(52) U.S. Cl.

CPC .............. *A61L 31/14* (2013.01); *A61F 2/915* (2013.01); *A61L 31/022* (2013.01); *A61F 2002/0081* (2013.01); *A61F 2210/0019* (2013.01); *A61F 2210/0076* (2013.01); *A61F 2250/0024* (2013.01)

(58) Field of Classification Search

CPC ...... A61F 2/04; A61F 2/06; A61F 2/82; A61F 2/915; A61F 2210/0019; A61F 2210/0076; A61F 2250/0024; A61F 2002/0081; A61L 31/14; A61L 31/022

See application file for complete search history.

(56) References Cited

U.S. PATENT DOCUMENTS

| | | | |
|---|---|---|---|
| 4,668,557 A | 5/1987 | Lakes | |
| 5,047,055 A | 9/1991 | Bao et al. | |
| 5,192,326 A | 3/1993 | Bao et al. | |
| 6,890,395 B2 | 5/2005 | Simhambhatla | |
| 8,277,719 B2 * | 10/2012 | Alderson | B29C 44/56 521/73 |
| 8,772,187 B2 | 7/2014 | Ugbolue et al. | |
| 9,241,808 B2 | 1/2016 | Sabatino | |
| 10,696,034 B2 | 6/2020 | Pattinson et al. | |
| 10,765,778 B2 | 9/2020 | Nappi | |

(Continued)

FOREIGN PATENT DOCUMENTS

| | | |
|---|---|---|
| EP | 2293746 | 3/2011 |
| EP | 3326582 | 9/2020 |

(Continued)

OTHER PUBLICATIONS

International Search Report and Written Opinion in International Appl. No. PCT/US22/75029, dated Nov. 23, 2022, 9 pages.

(Continued)

*Primary Examiner* — Dinah Baria

(74) *Attorney, Agent, or Firm* — Fish & Richardson P.C.

(57) ABSTRACT

A stent for insertion into a vessel of a patient includes an inner tube comprising a positive Poisson's ratio (PPR) material and defining a lumen extending along a longitudinal axis of the stent; and an outer tube comprising a negative Poisson's ratio (NPR) foam material and disposed around an entirety of the inner tube, the outer tube extending along the longitudinal axis of the stent. The stent is configured to exhibit an auxetic behavior in response to a deformation of the stent. An outer surface of the second portion is configured to apply a pressure to an inner surface of the vessel when the stent is implanted into the vessel and the deformation is removed.

24 Claims, 14 Drawing Sheets

(56) References Cited

U.S. PATENT DOCUMENTS

| | | | |
|---|---|---|---|
| 11,007,061 B2 | 5/2021 | Passman et al. | |
| 2006/0129227 A1 | 6/2006 | Hengelmolen | |
| 2006/0199876 A1 * | 9/2006 | Troczynski | A61L 31/086 523/115 |
| 2007/0213838 A1 | 9/2007 | Hengelmolen | |
| 2008/0071348 A1 | 3/2008 | Boismier et al. | |
| 2011/0029063 A1 | 2/2011 | Ma et al. | |
| 2017/0326274 A1 | 11/2017 | Nappi | |
| 2020/0085600 A1 | 3/2020 | Schwartz et al. | |

FOREIGN PATENT DOCUMENTS

| | | |
|---|---|---|
| WO | WO 2003/026494 | 4/2003 |
| WO | WO 2008/144728 | 11/2008 |
| WO | WO 2014/149854 | 9/2014 |
| WO | WO 2016/040613 | 3/2016 |
| WO | WO 2016/040615 | 3/2016 |
| WO | WO 2017/142968 | 8/2017 |
| WO | WO 2020/072349 | 4/2020 |
| WO | WO 2020/146777 | 7/2020 |
| WO | WO 2020/197854 | 10/2020 |
| WO | WO 2020/243768 | 1/2021 |
| WO | WO 2021/042044 | 3/2021 |
| WO | WO 2021/055939 | 3/2021 |

OTHER PUBLICATIONS

Griffith et al., "A multicenter retrospective study of the clinical results of the LINK SB Charitė intervertebral prosthesis. The initial European experience." Spine, Aug. 1994, 19(16): 1842-1849.

Healthline.com [online], "Is Acupuncture the Miracle Remedy for Everything?", Dec. 5, 2017, retrieved on Oct. 28, 2021, retrieved from URL <https://www.healthline.com/health/acupuncture-how-does-it-work-scientifically#how-does-it-work>, 44 pages.

Inamdar et al., Chapter 6: Chitosan and Low Molecular Weight Chitosan: Biological and Biomedical Applications, Advanced Biomaterials and Biodevices, 2014, pp. 147-182.

Kablitz et al., "Subcutaneous Peritoneal Catheter: 2½Years Experience," Artificial Organs, Aug. 1979, 3(3):210-214.

McAfee et al., "Failure of stabilization of the spine with methylmethacrylate. A retrospective analysis of twenty-four cases.", The Journal of Bone and Joint surgery. American Volume, Oct. 1986, 68(8):1145-1157.

Sirivisoot et al., "7—Orthopedic carbon nanotube biosensors for controlled drug delivery," Nanomedicine, Technologies and Applications, Woodhead Publishing Series in Biomaterials, 2012, pp. 149-179.

Waisbrod, "Treatment of metastatic disease of the spine with anterior resection and stabilization by means of a new cancellous metal construct," Archives of orthopaedic and traumatic surgery, Jun. 1988, 107:222-225.

Waldorff et al., "PEEK Titanium Composite (PTC) for Spinal Implants," Orthopedic Biomaterials, 2017, p. 427-465.

Yamamuro et al., "Replacement of the lumbar vertebrae of sheep with ceramic prostheses," The Journal of Bone and Joint Surgery, British vol. 1990,72B(5):889-893.

International Preliminary Report on Patentability in International Appln. No. PCT/US2022/075029, mailed on Feb. 29, 2024, 8 pages.

* cited by examiner

COMPOSITE POSITIVE AND NEGATIVE POISSON'S RATIO MATERIALS FOR MEDICAL DEVICES

BACKGROUND

The present disclosure relates generally to composite materials for and construction of various types of medical devices, including implantable medical devices, such as stents, spine discs, percutaneous device, and including needles.

Medical devices are used for various medical procedures that are performed by clinicians and the general population.

SUMMARY

We describe here medical devices, such as implantable medical devices and needles, that are formed of a composite of both Negative Poisson's Ratio (NPR) materials and Positive Poisson's Ratio (PPR) materials. For example, a material having a Poisson's ratio greater than zero, e.g., between 0 and 1 or between 0 and 0.5, is defined as a PPR material and a material having a Poisson's ratio between −1 and 0 is defined as an NPR material. Generally, the composite medical devices described herein exhibit an auxetic behavior when subject to a deformation. In some examples, the deformation is caused by a physical compression of the medical device and in some examples the deformation is caused by a thermal strain as part of a shape memory property. In some examples, the overall macroscopic behavior of the medical device is auxetic even when the medical device includes PPR materials. In some cases, the overall auxetic behavior is a consequence of using NPR materials within the medical device and, in some cases, the overall auxetic behavior is a consequence of using geometric patterns, such as re-entrant honeycomb patterns, that give rise to auxetic behavior.

In an aspect, a stent for insertion into a vessel of a patient includes an inner tube including a positive Poisson's ratio (PPR) material and defining a lumen extending along a longitudinal axis of the stent; and an outer tube including a negative Poisson's ratio (NPR) foam material and disposed around an entirety of the inner tube, the outer tube extending along the longitudinal axis of the stent. The stent is configured to exhibit an auxetic behavior in response to a deformation of the stent.

Embodiments can include one or any combination of two or more of the following features.

In some embodiments, the NPR foam material defines one or more pores on an outer surface of the outer tube.

In some embodiments, an outer surface of the outer tube is configured to apply a radial pressure to an inner wall of the vessel when the stent is disposed in the vessel and the deformation is removed.

In some embodiments, the deformation is caused by application of a compressive force along the longitudinal axis of the stent.

In some embodiments, at least one of the PPR material or the NPR material exhibits a shape memory property.

In some embodiments, the stent is configured to radially expand when exposed to a temperature of the vessel.

In some embodiments, the outer tube covers an entire length of an outer surface of the inner tube such that each axial end of the inner tube is flush with the corresponding axial end of the outer tube in a direction perpendicular to the longitudinal axis of the stent.

In some embodiments, the PPR material includes a metal alloy.

In some embodiments, the NPR foam material includes a titanium alloy. In some embodiments, the titanium alloy includes a titanium alloy that has been transformed from a non-auxetic titanium alloy to an auxetic titanium alloy. In some embodiments, the transformation of the titanium alloy is caused by a combination of compression and heat being applied to the non-auxetic titanium alloy.

In some embodiments, the stent includes a coating of a ceramic disposed on an outer surface of the outer tube.

In an aspect, a stent for insertion into a vessel of a patient includes a plurality of wires arranged in a geometric pattern, each wire of the plurality of wires including an inner cylindrical core and an outer tube disposed around the inner cylindrical core, each inner cylindrical core including a PPR material and each outer tube including an NPR foam material. The wherein the stent is configured to exhibit an auxetic behavior in response to a deformation of the stent.

Embodiments can include one or any combination of two or more of the following features.

In some embodiments, an outer surface of each outer tube is configured to apply a radial pressure to an inner surface of the vessel when the auxetic stent is disposed in the vessel.

In some embodiments, the NPR foam material defines one or more pores on an outer surface of the outer tube.

In some embodiments, the PPR material includes a metal alloy.

In some embodiments, at least one of the PPR material or the NPR material exhibits a shape memory property.

In some embodiments, the auxetic stent is configured to radially expand when exposed to a temperature of the vessel.

In some embodiments, the geometric pattern is a geometric pattern of re-entrant honeycombs configured to invoke the auxetic behavior of the stent in response to the deformation.

In some embodiments, the NPR foam material includes a titanium alloy that has been transformed from a non-auxetic titanium alloy to an auxetic titanium alloy.

In an aspect, an implantable medical device for implantation into an anatomical structure includes a first cylindrical portion including a PPR material; and a second cylindrical portion including an NPR foam material defining pores, the second cylindrical portion disposed around an entirety of the first cylindrical portion or disposed within the first cylindrical portion. The implantable medical device is configured to exhibit an auxetic behavior in response to a deformation of the implantable medical device.

Embodiments can include one or any combination of two or more of the following features.

In some embodiments, an outer surface of the second cylindrical portion is configured to apply a pressure to an inner surface of the anatomical structure when the implantable medical device is implanted in the anatomical structure and the deformation is removed.

In some embodiments, the implantable medical device includes a plurality of wires and each wire of the plurality of wires includes a respective first cylindrical portion and second cylindrical portion.

In some embodiments, at least one of the PPR material or the NPR foam material exhibits a shape memory property.

In some embodiments, the anatomical structure includes a vessel, an organ, a skin, or a vertebrae.

In some embodiments, the implantable medical device includes an auxetic stent, an auxetic spine disc, or an auxetic percutaneous device.

In an aspect, an auxetic spine disc includes a first portion including an NPR foam material. The first portion defines a recess extending around an entire perimeter of the first portion. The NPR foam material includes one or more pores on at least two outer surfaces of the first portion. The auxetic spine disc includes a second portion that includes a PPR material disposed within the recess of the first portion. An overall behavior of the auxetic spine disc is auxetic in response to a deformation of the auxetic spine disc. One of the at least two outer surfaces of the first portion is configured to apply a pressure to a first vertebrae body and the other of the at least two outer surfaces is configured to apply an opposing pressure to a second vertebrae body when the auxetic spine disc is implanted between the first vertebrae body and the second vertebrae body. The pressure causes the deformation.

Embodiments can include one or any combination of two or more of the following features.

In some embodiments, the applied pressure facilitates a growth of tissue from both the first vertebrae body and the second vertebrae body into the one or more pores when the spine disc is implanted between the first vertebrae body and the second vertebrae body.

In some embodiments, the NPR foam material is made of a titanium alloy that has been transformed from a non-auxetic titanium alloy to an auxetic titanium alloy.

In some embodiments, the PPR material includes a metal alloy. In some cases, the PPR material includes a titanium alloy.

In some embodiments, at least one of the PPR material or the NPR material exhibits a shape memory property. In some embodiments, the PPR material includes Nitinol. In some embodiments, the shape memory property causes the auxetic spine disc to expand when exposed to a temperature of a patient.

In some embodiments, the auxetic spine disc is stiffer in a normal direction than in a transverse direction.

In some embodiments, the first portion and the second portion are both circular.

In some embodiments, each of the at least two outer surfaces of the first portion includes a coating of a ceramic material. In some embodiments, the coating is hydroxyapatite.

In an aspect, an auxetic percutaneous device includes a cylindrical portion that includes a PPR material. The cylindrical portion defines a cylindrical recess extending radially inward from an outer diameter of the first cylindrical portion. The cylindrical portion defines a lumen extending through the cylindrical portion in a direction of a longitudinal axis. The auxetic percutaneous device includes a foam layer including a NPR foam material disposed along a path spanning at least three sides of the recess. The foam layer includes one or more pores on an outer surface of the foam layer. An overall behavior of the auxetic percutaneous device is auxetic in response to a deformation of the auxetic percutaneous device. The outer surface of the foam layer is configured to apply a pressure to an inner surface of a skin when the auxetic percutaneous device is implanted into the skin and the deformation is removed.

Embodiments can include one or any combination of two or more of the following features.

In some embodiments, the applied pressure facilitates a growth of tissue from the skin into the one or more pores.

In some embodiments, at least one of the PPR material or the NPR foam material exhibits a shape memory property. In some embodiments, the shape memory property causes the deformation of the auxetic percutaneous device such that the auxetic percutaneous device radially expands when exposed to a temperature of the skin.

In some embodiments, the skin does not contact the cylindrical portion when the auxetic percutaneous device is implanted into the skin.

In some embodiments, the skin only contacts the foam layer when the auxetic percutaneous device is implanted into the skin.

In some embodiments, the skin includes at least two layers of skin and each layer of skin contacts the foam layer when the auxetic percutaneous device is implanted into the skin.

In some embodiments, the PPR material includes a metal alloy.

In some embodiments, the NPR foam material is made of a titanium alloy that has been transformed from a non-auxetic titanium alloy to an auxetic titanium alloy.

In some embodiments, the outer surface of the foam layer includes a coating of a ceramic material. In some embodiments, the coating is hydroxyapatite.

In some embodiments, the foam layer is disposed along each face of the cylindrical recess.

In some embodiments, the foam layer covers each face of the cylindrical recess.

In some embodiments, the foam layer spans circumferentially around an entire circumference of the cylindrical portion.

In some embodiments, the PPR material is a metal alloy. In some embodiments, the PPR material is Nitinol.

In some embodiments, the deformation is caused by a compression along the longitudinal axis.

In an aspect, an auxetic acupuncture needle includes a cylindrical body that includes a PPR material. The cylindrical body includes a first end along a longitudinal axis. The first end defines a tapered tip region configured to penetrate one or more layers of a skin. The cylindrical body being electrically connectable to a piezoelectric energy source for providing electrical energy through the cylindrical body for providing electrotherapy treatment to the one or more layers of the skin. The auxetic acupuncture needle including a metal foam portion that includes an NPR material. The metal foam portion being disposed within a circumferential recess of the cylindrical body around the longitudinal axis. The circumferential recess spanning along the cylindrical portion of the cylindrical body. The foam portion configured to expand to provide an increased surface area. The electrical energy is configured to be transferred from the metal foam portion to the one or more layers of the skin through a majority of the increased surface area.

Embodiments can include one or any combination of two or more of the following features.

In some embodiments, the metal foam portion is made of a titanium alloy that has been transformed from a non-auxetic titanium alloy to an auxetic titanium alloy.

In some embodiments, the acupuncture needle includes a coating of a ceramic material. In some embodiments, the ceramic material is hydroxyapatite.

In some embodiments, the PPR material is a stainless steel alloy.

In an aspect, an electroacupuncture system includes a piezoelectric energy source and a plurality of auxetic acupuncture needles. Each auxetic acupuncture needle includes a cylindrical body that includes a PPR material. The cylindrical body includes a first end along a longitudinal axis. The first end defines a tapered tip region configured to penetrate one or more layers of a skin. The cylindrical body being electrically connectable to a piezoelectric energy source for providing electrical energy through the cylindrical body for providing electrotherapy treatment to the one or more layers of the skin. Each auxetic acupuncture needle includes a metal foam portion that includes a NPR material. The metal foam portion being disposed within a circumferential recess of the cylindrical body around the longitudinal axis. The circumferential recess spanning along the cylindrical portion of the cylindrical body. The metal foam portion configured to expand to provide an increased surface area. The electrical energy is configured to be transferred from the metal foam portion to the one or more layers of the skin through a majority of the increased surface area.

Embodiments can include one or any combination of two or more of the following features.

In some embodiments, the metal foam portion is made of a titanium alloy that has been transformed from a non-auxetic titanium alloy to an auxetic titanium alloy.

In some embodiments, the auxetic acupuncture needles include a coating of a ceramic material. In some embodiments, the ceramic material is hydroxyapatite.

In some embodiments, the PPR material is a stainless steel alloy.

In an aspect, a method for transferring electrical energy to one or more tissues of a patient is described. The method includes generating, using a piezoelectric energy source, electrical energy. The method includes transferring, via one or more wires, the generated electrical energy from the piezoelectric source to a cylindrical body of an auxetic acupuncture needle. The cylindrical body includes a PPR material. The method includes transferring, via mechanical contact, the generated electrical energy from the cylindrical body to a metal foam portion of the auxetic acupuncture needle. The metal foam portion includes an NPR material. The method includes transferring, via mechanical contact, the generated electrical energy from the metal foam portion to the one or more tissues of the patient.

Embodiments can include one or any combination of two or more of the following features.

In some embodiments, the method includes increasing a surface area of the outer surface of the metal foam portion.

In some embodiments, the method includes transforming a PPR material into an NPR material to form the metal foam portion. In some embodiments, the transformation results in an increased surface area of the outer surface of the metal foam portion.

In some embodiments, a majority of entire surface area of the outer surface of the metal foam portion is used to transfer the electrical energy to the patient.

While the above features are described with reference to specific aspects of this disclosure, any of the above features can be used with any of the above aspects.

Other embodiments are within the scope of the claims.

DETAILED DESCRIPTION

We describe here medical devices, such as implantable medical devices and needles, that are formed of a composite of both Negative Poisson's Ratio (NPR) materials and Positive Poisson's Ratio (PPR) materials. A material having a Poisson's ratio greater than zero, e.g., between 0 and 1 or between 0 and 0.5, is defined as a PPR material and a material having a Poisson's ratio between −1 and 0 is defined as an NPR material. Generally, the composite medical devices described herein exhibit an auxetic behavior in response to a deformation. An auxetic material is a material that exhibits a negative Poisson's ratio. For instance, when an auxetic material is stretched in one direction, the material expands in a direction perpendicular to the applied stretching force; and when an auxetic material is compressed in one direction, the material contracts in a direction perpendicular to the applied compression. In some examples, the deformation of the composite medical devices described here is caused by a physical compression of the medical device. In some examples the deformation is caused by a thermal strain that arises from a shape memory property of the medical device. In some examples, the overall behavior of the medical device is auxetic even when the medical device includes PPR materials. In some cases, the overall auxetic behavior is a consequence of using NPR materials within the medical device. In some cases, the overall auxetic behavior is a consequence of the presence of geometric patterns, such as re-entrant honeycomb patterns, that give rise to auxetic behavior.

Figure 1A:
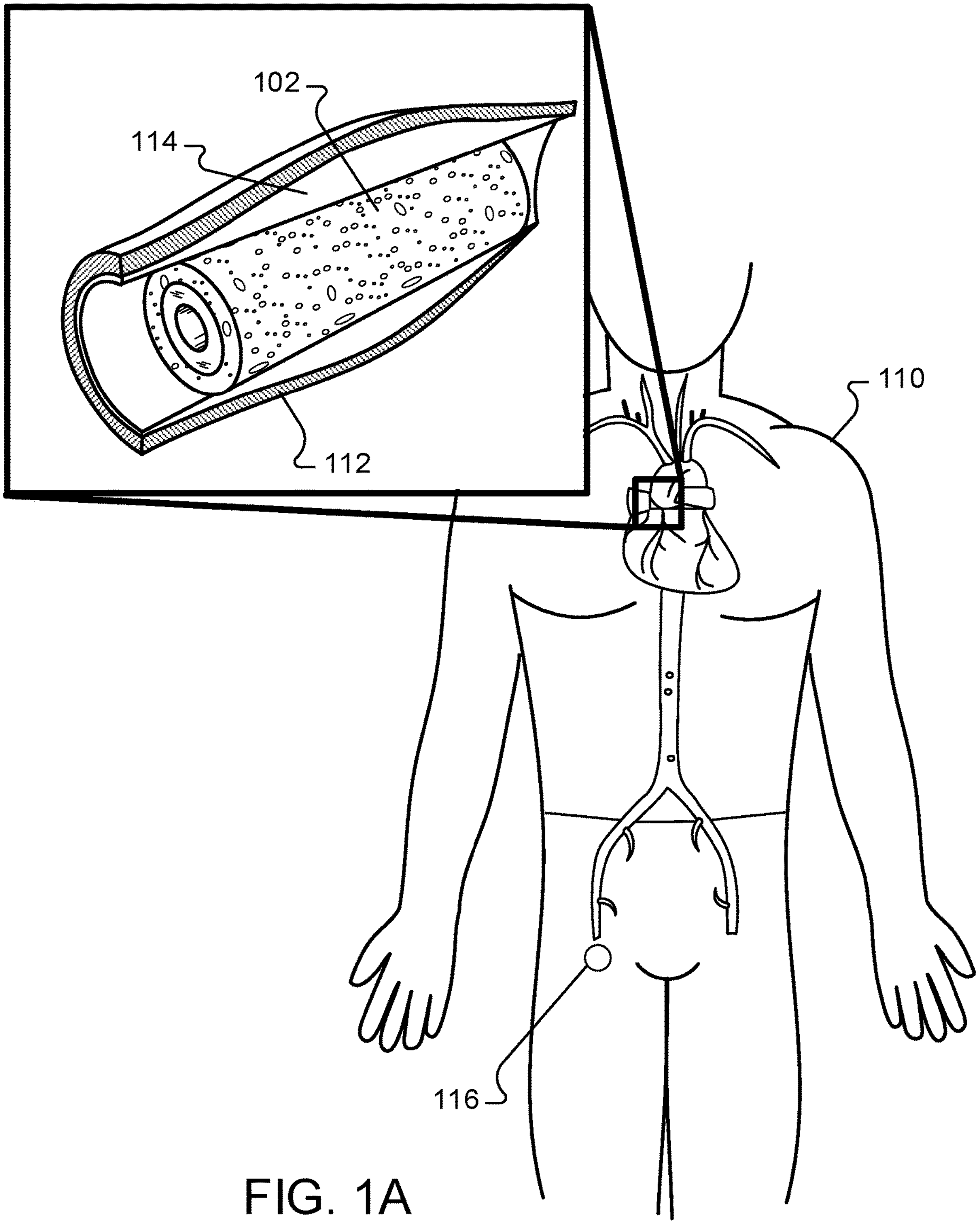
FIG. 1A is an illustration of an auxetic stent in a vessel of a patient.

FIG. 1A is an illustration of an auxetic stent 102 disposed in a vessel 112 of a patient 110. In this example, the vessel 112 is an artery but the vessel 112 can also be a vein or another vessel of the patient 110. In the example shown, the patient 110 is undergoing an angioplasty procedure. In this example, a surgeon (not shown) makes an incision 116 into the skin of the patient 110 and inserts the auxetic stent 102 into the vessel 112 (here, an artery) of the patient 110 through the incision 116. The surgeon navigates the auxetic stent 102 to an implantation site within the vessel 112. In this example, the implantation site is located in a coronary artery that has a clot 114 (e.g., a thrombosis).

Figure 1B:
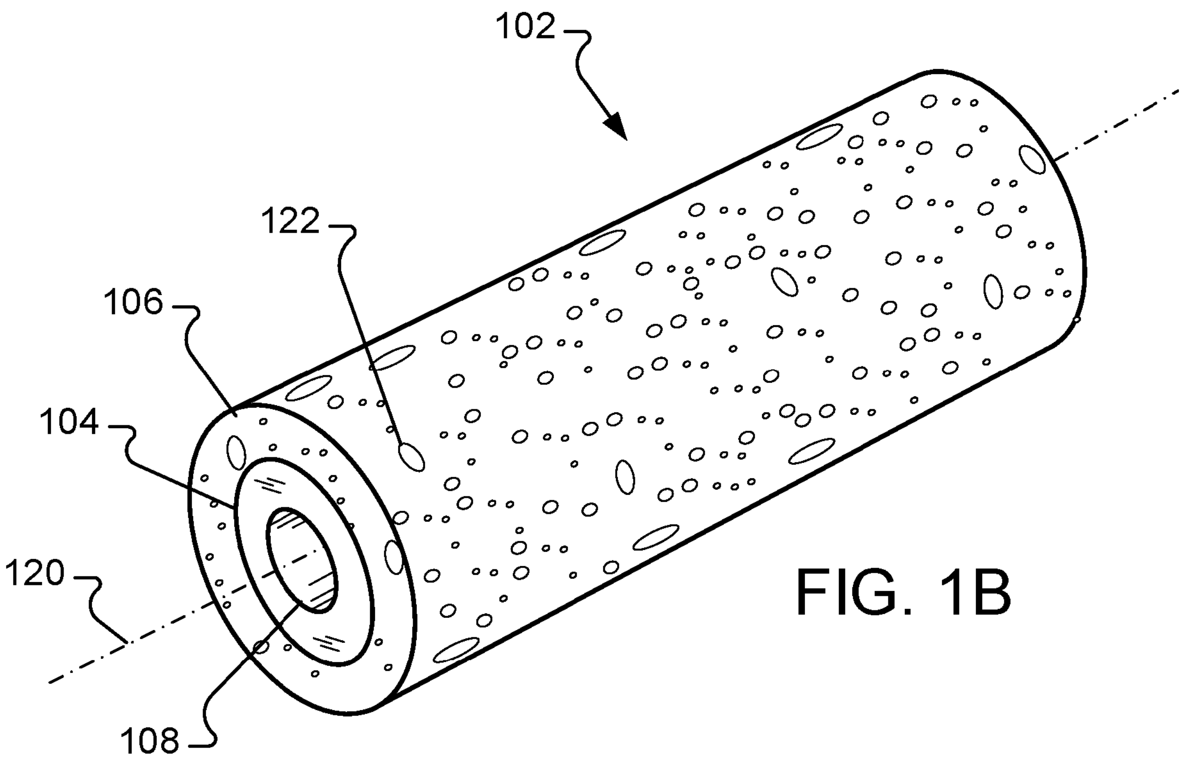
FIG. 1B is a perspective view of the auxetic stent of FIG. 1A.
Figure 1C:
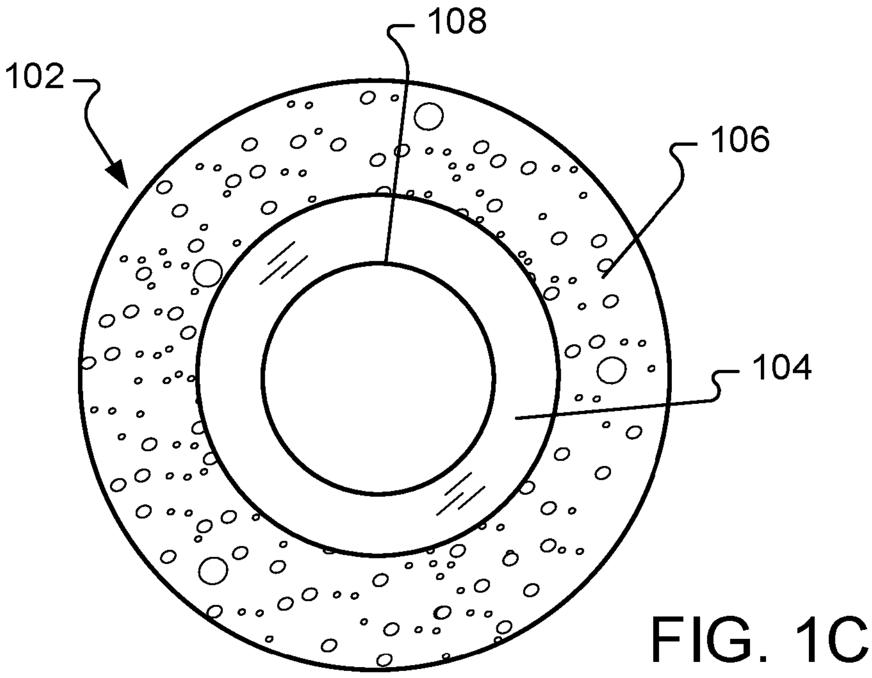
FIG. 1C is a cross-sectional view of the auxetic stent of FIG. 1A.

FIGS. 1B and 1C are a perspective view and a cross-sectional view, respectively, of the auxetic stent 102. As used herein, an "auxetic stent" means that at least a portion of the stent exhibits an auxetic behavior when subject to a deformation (e.g., mechanical, thermal, etc.). In some cases, the presence of an NPR material in the auxetic stent causes the auxetic behavior. In some cases, a geometric pattern present in the material of the auxetic stent causes the auxetic behavior. And in some cases, a combination of both an NPR material and a geometric pattern causes the auxetic behavior.

The auxetic stent 102 includes an inner cylindrical portion 104. In some examples, the inner cylindrical portion 104 is made of a PPR material, e.g., a biocompatible PPR material. In some examples, the PPR material is a metal alloy such as stainless steel or a titanium alloy, e.g., a nickel-titanium alloy (e.g., Nitinol). In some examples, the inner cylindrical portion 104 is a metal foam.

The inner cylindrical portion 104 is an inner tube that defines a lumen 108 that extends along a longitudinal axis 120 of the auxetic stent 102. The lumen 108 allows blood to flow through the auxetic stent 102 when the auxetic stent 102 is implanted at the implantation site (e.g., in the vessel 112 of the patient 110).

The auxetic stent 102 includes an outer cylindrical portion 106. The outer cylindrical portion 106 is an outer tube that is disposed around an entirety of the inner cylindrical portion 104. The outer cylindrical portion 106 also encircles the entire auxetic stent 102 so that the vessel 112 only contacts the outer cylindrical portion 106 of the stent (e.g., the vessel 112 does not contact the inner cylindrical portion 104 because it is shielded by the outer cylindrical portion 106). In some examples, the outer cylindrical portion 106 covers an entire length of an outer surface of the inner cylindrical portion 104 such that each axial end of the inner portion 104 is flush with the corresponding axial end of the outer portion 106 in a direction perpendicular to the longitudinal axis 120.

In some examples, the auxetic stent 102 has a length (e.g., measured along the longitudinal axis 120) of between 5 and 50 mm and a diameter (e.g., measured perpendicular to the longitudinal axis 120) of between 2.5 and 4.0 mm. In a specific example, the auxetic stent 102 has a length of 20 mm and a diameter of between 3.0 mm. In some examples, the auxetic stent 102 is a ureteral stent with a length up to 300 mm, e.g., between 200 mm and 300 mm.

In some examples, the outer cylindrical portion 106 of the auxetic stent 102 includes an NPR foam material composed of, e.g., polymer, ceramic, metal NPR material, or combinations thereof. In some examples, the NPR foam material is made of a biocompatible titanium alloy (e.g., Ti6Al4V). In some examples, the outer cylindrical portion 106 is formed of a material that has been transformed from a material exhibiting PPR behavior (a "non-auxetic material) to a material exhibiting NPR behavior (an "auxetic material") (e.g., by a combination of heat and pressure as described with reference to FIG. 8 below). In a specific example, the outer cylindrical portion 106 of the auxetic stent 102 is formed of a titanium alloy that has been transformed from a non-auxetic titanium alloy to an auxetic titanium alloy, e.g., by application of heat, compressive pressure, or both to the non-auxetic titanium alloy.

The NPR foam material defines one or more pores 122 disposed on an outer surface of the outer cylindrical portion 106. The pores 122 define recesses (or void space) within the outer cylindrical portion 106. As shown in FIG. 1B, the one or more pores 122 can be of various shapes and sizes. For example, the pores 122 can be circular-shaped or elliptical-shaped. In some examples, the one or more pores 122 can be of various depths into the outer cylindrical portion 106.

The auxetic stent 102 exhibits an overall auxetic behavior in response to the deformation of the auxetic stent 102. As used herein "an overall auxetic behavior" means that the behavior of the auxetic stent 102 is auxetic. For example, when the auxetic stent 102 is compressed along its longitudinal axis 120 (e.g., when a surgeon squeezes the ends of the auxetic stent 102 together), the outer diameter of the outer cylindrical portion 106 decreases. Likewise, if the auxetic stent 102 is extended along the longitudinal axis 120 (e.g., when a surgeon pulls on each end of the auxetic stent 102), the outer diameter of the outer cylindrical portion 106 increases. In these cases, the deformation can be caused either by the surgeon physically compressing the auxetic stent 102 or through the use of a temperature gradient that causes a deformation, e.g., by taking advantage of a shape memory property of the stent. Further details regarding the deformation is described with reference to FIGS. 2A and 2B below.

The auxetic stent 102 can exhibit an overall auxetic behavior despite including PPR materials. For example, when the inner cylindrical portion 104 includes a PPR material and the outer cylindrical portion 106 includes an NPR material, the overall behavior of the auxetic stent 102 can still be auxetic. In some cases, the auxetic stent 102 is designed by accounting for the competing behaviors of NPR and PPR materials. For example, the auxetic stent 102 can be designed using continuum mechanics theory or using a finite element model. In some examples, the overall behavior of the auxetic stent 102 is auxetic when the outer cylindrical portion 106 includes a NPR material and the inner cylindrical portion 104 includes a PPR material and when the outer cylindrical portion 106 has a thickness (e.g., measured in the radial direction) that is larger than a thickness of the inner cylindrical portion 104.

Figure 1D:
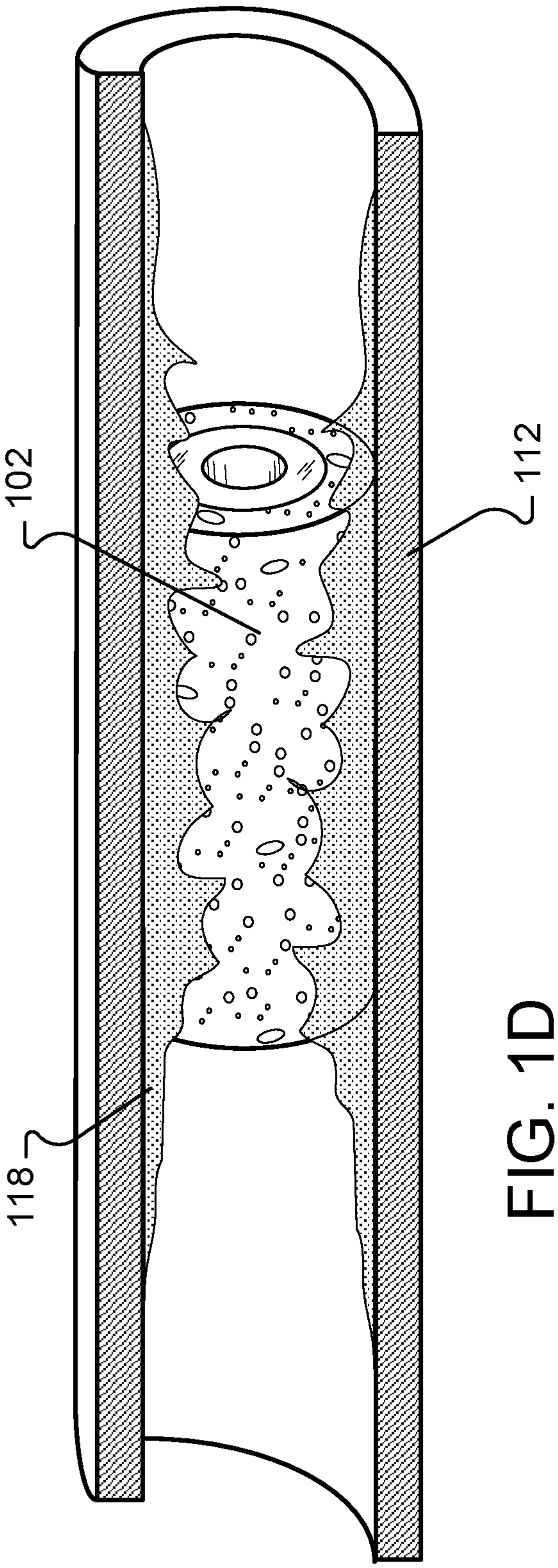
FIG. 1D is a perspective view of the auxetic stent of FIG. 1A when implanted into the patient illustrating an in-growth of tissue into the auxetic stent.

FIG. 1D is a perspective view of the auxetic stent 102 when implanted into the vessel 112. When the auxetic stent 102 is implanted into the vessel 112, the diameter of the auxetic stent 102 radially expands which causes an outer surface of the outer cylindrical portion 106 to apply a radial pressure to an inner surface of the vessel 112. For example, the auxetic stent 102 can radially expand in the vessel 112 due to a shape memory property of the stent (e.g., when either or both of the inner cylindrical portion 104 and the outer cylindrical portion 106 includes Nitinol). In some examples, this shape memory property is invoked when the auxetic stent 102 experiences an increased temperature of the vessel 112 compared to the ambient temperature external to the patient 110. In these examples, the auxetic stent 102 increases in diameter as a function of time and eventually contacts the inner surface of the vessel 112 to gradually apply radial pressure to the inner surface of the vessel 112.

The applied pressure facilitates a growth of tissue from the inner surface of the vessel into the one or more pores 122 when the auxetic stent 102 is implanted into the vessel 112. For example, the pores can enhance tissue growth into the auxetic stent 102 causing a majority of the surface area of the outer cylindrical portion 106 to attach to the inner surface of the vessel 112.

In some examples, the auxetic stent 102 includes a coating of a ceramic material (e.g., hydroxyapatite). For example, all or a portion of the outer cylindrical portion 106 can include a coating of hydroxyapatite. For example, the outer surface of the outer cylindrical portion 106 can include a coating of hydroxyapatite. In some examples, hydroxyapatite provides improved biocompatibility compared to an uncoated auxetic stent.

Figure 2A:
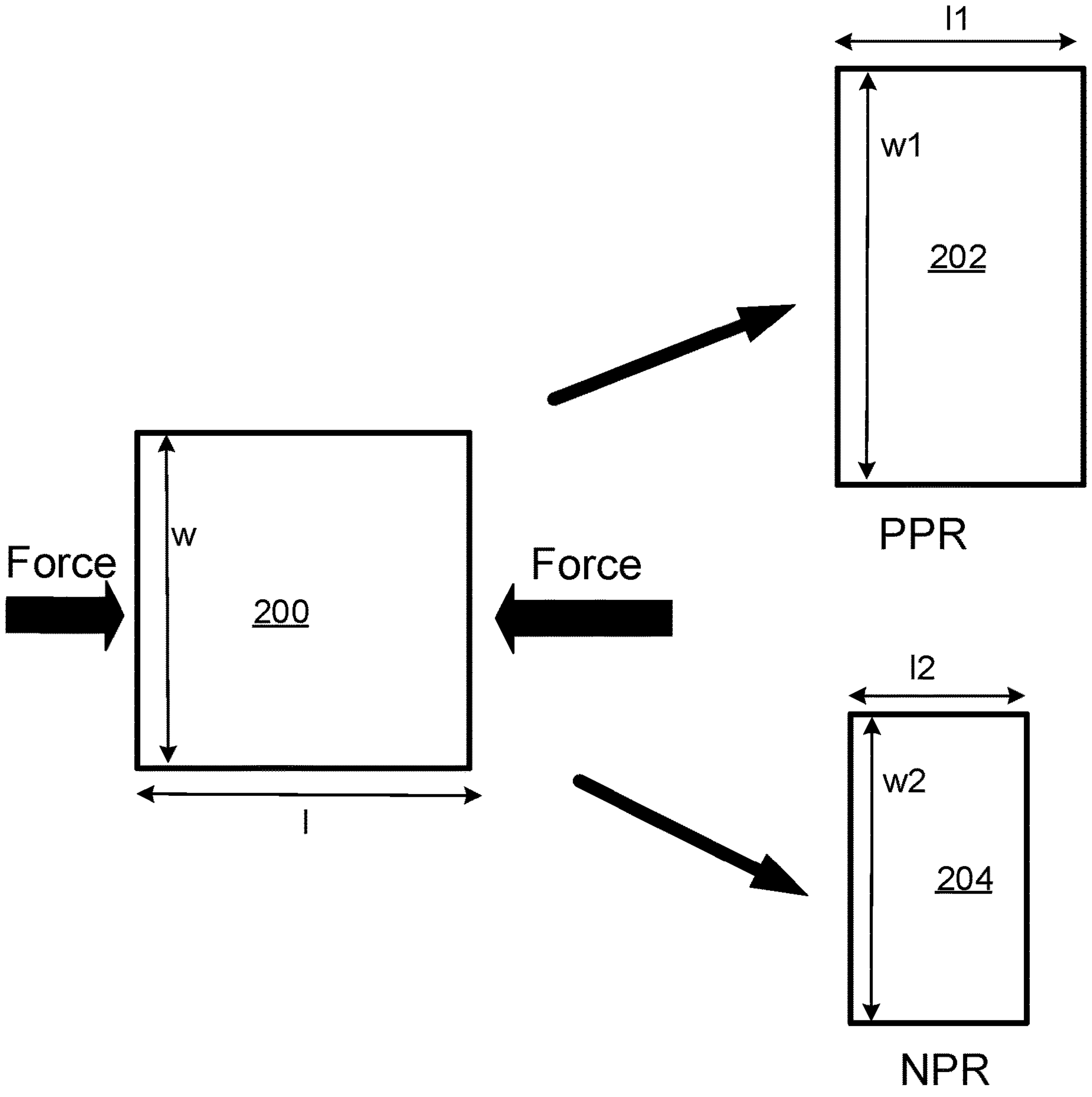
FIG. 2A is an illustration of the mechanics of an auxetic stent.

FIG. 2A is an illustration of the mechanics of the auxetic stent 102. As noted above, an NPR material is a material that has a Poisson's ratio that is less than zero, such that when the material experiences a positive strain along one axis (e.g., when the material is stretched), the strain in the material along the two perpendicular axes is also positive (e.g., the material expands in cross-section). Conversely, when the material experiences a negative strain along one axis (e.g., when the material is compressed), the strain in the material along a perpendicular axis is also negative (e.g., the material compresses along the perpendicular axis).

By contrast, a PPR material has a Poisson's ratio that is greater than zero. When a PPR material experiences a positive strain along one axis (e.g., when the material is stretched), the strain in the material along the two perpendicular axes is negative (e.g., the material compresses in cross-section), and vice versa. Materials with negative and positive Poisson's ratios are illustrated in FIG. 2A, which depicts a hypothetical two-dimensional block of material 200 with length l and width w.

If the hypothetical block of material 200 is a PPR material, when the block of material 200 is compressed along its width w, the material deforms into the shape shown as block 202. The width w1 of block 202 is less than the width w of block 200, and the length l1 of block 202 is greater than the length l of block 200: the material compresses along its width and expands along its length.

By contrast, if the hypothetical block of material 200 is an NPR material, when the block of material 200 is compressed along its width w, the material deforms into the shape shown as block 204. Both the width w2 and the length l2 of block 204 are less than the width w and length l, respectively, of block 200: the material compresses along both its width and its length.

NPR materials for medical devices can be foams, such as polymeric foams, ceramic foams, metal foams, or combinations thereof. A foam is a multi-phase composite material in which one phase is gaseous and the one or more other phases are solid (e.g., polymer, ceramic, or metal). Foams can be closed-cell foams, in which each gaseous cell is sealed by solid material; open-cell foams, in which the each cell communicates with the outside atmosphere; or mixed, in which some cells are closed and some cells are open.

An example of an NPR foam structure is a re-entrant structure, which is a foam in which the walls of the cells are concave, e.g., protruding inwards toward the interior of the cells. In a re-entrant foam, compression applied to opposing walls of a cell will cause the four other, inwardly directed walls of the cell to buckle inward further, causing the material in cross-section to compress, such that a compression occurs in all directions. Similarly, tension applied to opposing walls of a cell will cause the four other, inwardly directed walls of the cell to unfold, causing the material in cross-section to expand, such that expansion occurs in all directions.

NPR foams can have a Poisson's ratio of between −1 and 0, e.g., between −0.8 and 0, e.g., −0.8, −0.7, −0.6, −0.5, −0.4, −0.3, −0.2, or −0.1. NPR foams can have an isotropic Poisson's ratio (e.g., Poisson's ratio is the same in all directions) or an anisotropic Poisson's ratio (e.g., Poisson's ratio when the foam is strained in one direction differs from Poisson's ratio when the foam is strained in a different direction).

An NPR foam can be polydisperse (e.g., the cells of the foam are not all of the same size) and disordered (e.g., the cells of the foam are randomly arranged, as opposed to being arranged in a regular lattice). An NPR foam can have a characteristic dimension (e.g., the size of a representative cell, such as the width of the cell from one wall to the opposing wall) ranging from 0.1 μm to about 3 mm, e.g., about 0.1 μm, about 0.5 μm, about 1 μm, about 10 μm, about 50 μm, about 100 μm, about 500 μm, about 1 mm, about 2 mm, or about 3 mm.

Examples of polymeric foams for medical devices include thermoplastic polymer foams (e.g., polyester polyurethane or polyether polyurethane); viscoelastic elastomer foams; or thermosetting polymer foams such as silicone rubber. Examples of metal foams for medical devices include metal foams based on copper, aluminum, or other metals, or alloys thereof.

NPR-PPR composite materials are composites that include both regions of NPR material and regions of PPR material. NPR-PPR composite materials can be laminar composites, matrix composites (e.g., metal matrix composites, polymer matrix composites, or ceramic matrix composites), particulate reinforced composites, fiber reinforced composites, or other types of composite materials. In some examples, the NPR material is the matrix phase of the composite and the PPR material is the reinforcement phase, e.g., the particulate phase or fiber phase. In some examples, the PPR material is the matrix phase of the composite and the NPR material is the reinforcement phase.

Figure 2B:
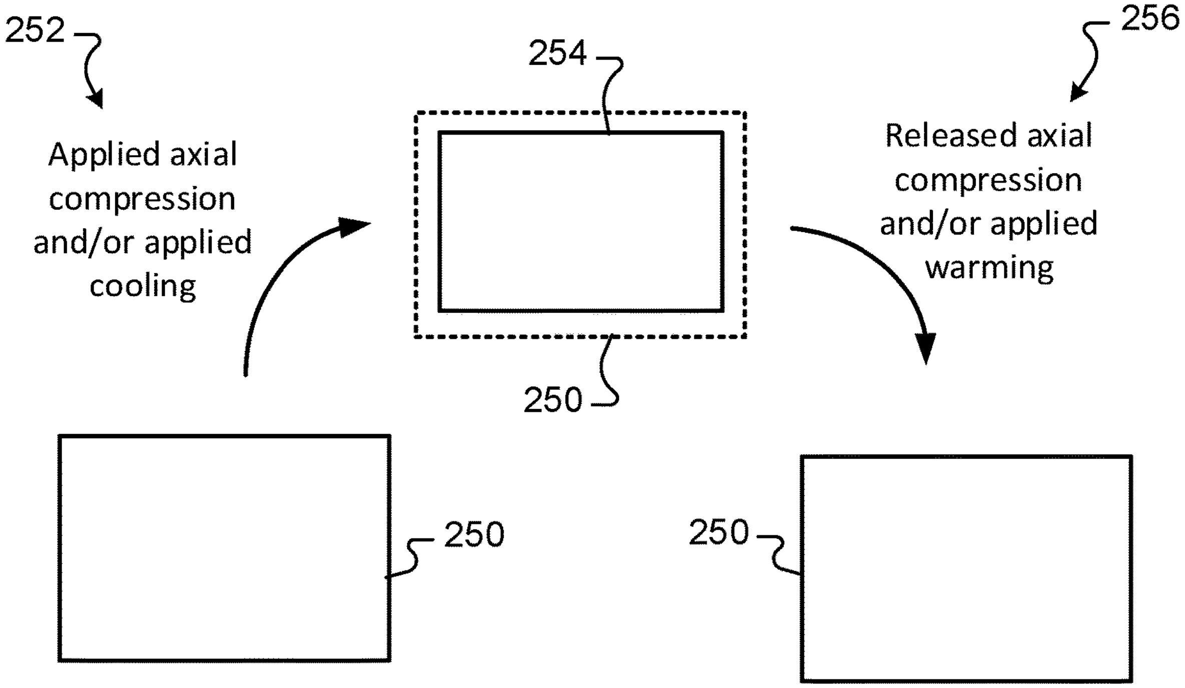
FIG. 2B is an illustration of the mechanics of an auxetic stent.

FIG. 2B is an illustration of the mechanics of the auxetic stent 102 when made of one or more shape memory alloys (e.g., Nitinol). A shape memory material is a material that can be deformed from a first deformation state to a second deformation state but then can revert to its first deformation state, e.g., upon application of a stimulus such as compression or heat. For example, at least one of the inner cylindrical portion 104 or the outer cylindrical portion 106 can include a material having a shape memory property. For example, either or both of an PPR material or an NPR material can exhibit a shape memory property.

The shape memory property can cause the auxetic stent 102 to radially contract from a first deformation state to a second deformation state when cooled prior to being implanted into the vessel 112. The shape memory property can cause the auxetic stent 102 to radially expand from the second deformation state back to the first deformation state when exposed to a temperature of the vessel 112.

A schematic of the auxetic stent 102 at an "initial condition" is represented by the box 250. As used herein, "initial condition" means that the auxetic stent 102 is at an ambient temperature condition and no deformations or forces are applied to the auxetic stent 102 at this point other than environmental effects (e.g., gravity, atmospheric pressure, etc. are incorporated into the initial condition). The auxetic stent 102 represented by box 250 is at a first deformation state.

At step 252, an axial compression and/or thermal cooling is applied to the auxetic stent 102 (e.g., by physically compressing the auxetic stent 102, by placing the auxetic stent 102 in a cooler, such as a refrigerator, etc.), causing the auxetic stent 102 to change from the first deformation state at box 250 to a second deformation state at box 254. In this example, and as noted above with reference to FIG. 2A, the auxetic stent 102 both radially contracts and axially contracts when the overall behavior of the auxetic stent 102 is auxetic.

At step 256, the axial compression applied in step 252 is released and/or thermal warming is applied to the auxetic stent 102 (e.g., by physically releasing the auxetic stent 102, by placing the auxetic stent 102 in a heater, such as an oven, etc.) causing the auxetic stent 102 to change from the second deformation state at box 254 back to the first deformation state again represented by box 250. In this example, and as noted above with reference to FIG. 2A, the auxetic stent 102 both radially expands and axially expands when the overall behavior of the auxetic stent 102 is auxetic.

In some examples, a surgeon causes the auxetic stent 102 to change from the first deformation state at box 250 to the second deformation state at box 254 by cooling the auxetic stent 102. This causes a reduction in an overall dimension of the auxetic stent 102. The surgeon then inserts the auxetic stent 102 through the incision site 116 of the patient 110 and navigates the auxetic stent 102 to the implantation site within the vessel 112. Once the auxetic stent 102 is at the implantation site in the vessel 112, the body temperature of the patient 110 warms the auxetic stent 102 which causes the auxetic stent 102 to change from the second deformation state at box 254 back to the first deformation state at box 250. This results in an increase in an overall diameter of the auxetic stent 102 which cause the pressure to be applied to the inner surface of the vessel 112. In this way, the auxetic stent 102 is deformed by a temperature difference between the ambient conditions external to the patient 110 and the body temperature of the patient 110.

Figure 3A:
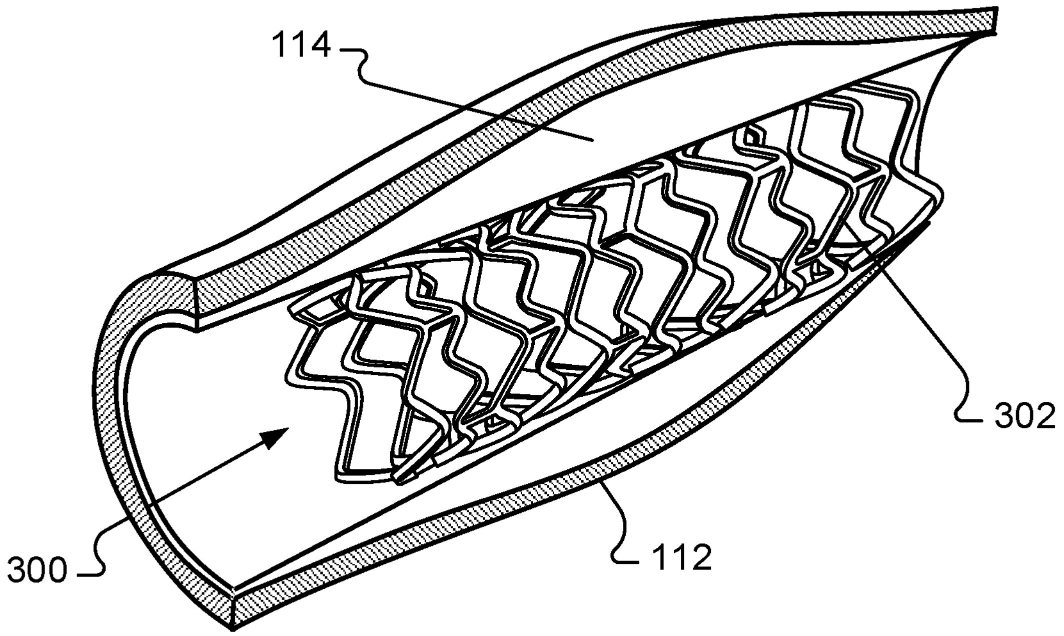
FIG. 3A is perspective view of an auxetic stent with a plurality of wires.
Figure 3B:
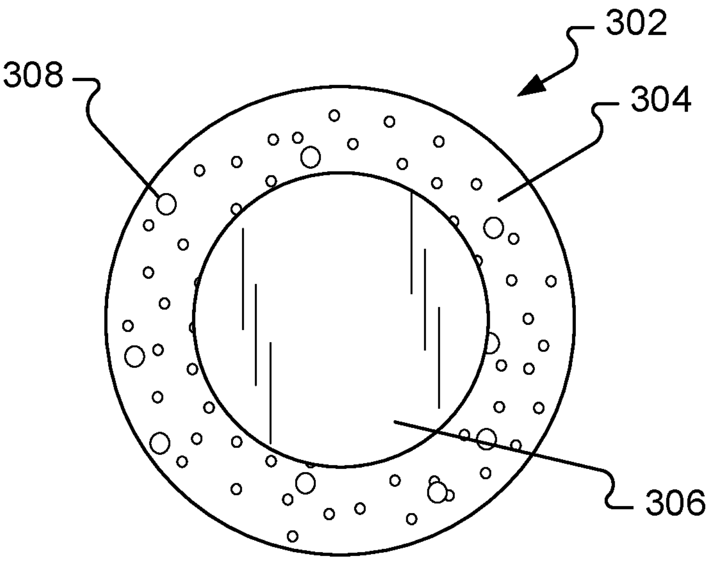
FIG. 3B is cross-sectional view of the auxetic stent of FIG. 3A.

FIGS. 3A and 3B are perspective views and cross-sectional views of an auxetic stent 300 with a plurality of wires 302. Auxetic stent 300 is similar to auxetic stent 102 in that at least one portion of the auxetic stent 300 exhibits an auxetic behavior in response to a deformation of the auxetic stent 300.

Figure 3C:
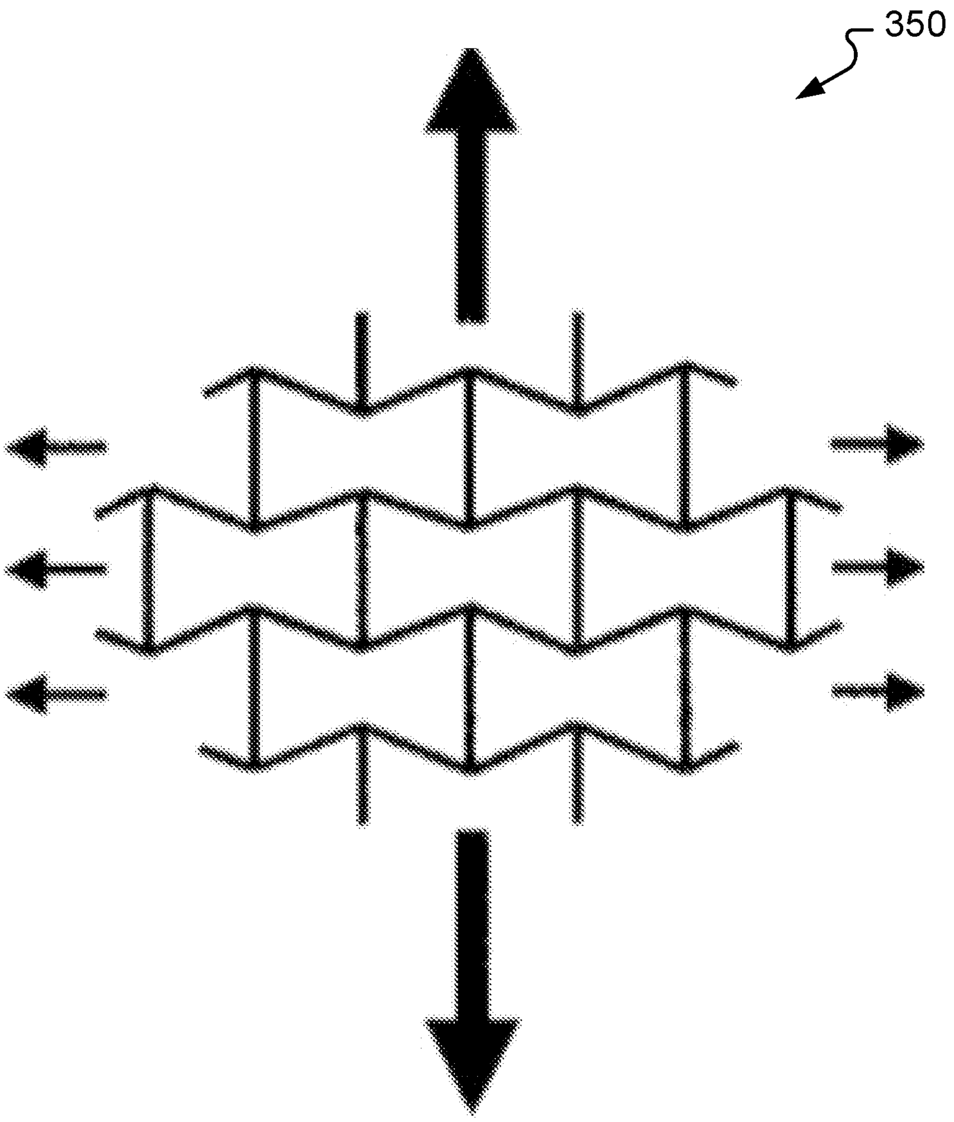
FIG. 3C is a schematic of a re-entrant honeycomb geometric pattern.

In this example, the plurality of wires 302 are arranged in a geometric pattern. In some examples, the geometric pattern is the geometric pattern of re-entrant honeycombs 350 as shown in FIG. 3C. As shown in FIG. 3C, when the auxetic stent is expanded in one direction (e.g., the axial direction), the auxetic stent also expands in an orthogonal direction (e.g., the radial direction). In some examples, the plurality of wires 302 define a mesh scaffolding.

Each wire 302 of the plurality of wires 302 includes an inner cylindrical portion 306 and an outer cylindrical portion 304 disposed around the inner cylindrical portion 306 of each wire 302. The inner cylindrical portion 306 is similar to the inner cylindrical portion 104 of the auxetic stent 102 (described above with reference to FIGS. 1A-2B) except the inner cylindrical portion 306 does not define a lumen therethrough. Instead, the inner cylindrical portion 306 is a solid cylinder that forms an inner core of each wire 302. In this example, the inner cylindrical portion 306 includes a PPR material, such as a biocompatible PPR material. Like the inner cylindrical portion 104, the inner cylindrical portion 306 can include a metal alloy such as stainless steel or a titanium alloy, e.g., a nickel-titanium alloy (e.g., Nitinol) that exhibits a non-auxetic behavior in response to a deformation of the auxetic stent 300. In some examples, the inner cylindrical portion 306 is a metal foam.

The outer cylindrical portion 304 is similar to the outer cylindrical portion 106 of the auxetic stent 102 (described above with reference to FIGS. 1A-2B) except the outer cylindrical portion 304 does not encircle the entire auxetic stent 300. Instead, the outer cylindrical portion 305 is disposed around an entirety of each inner cylindrical portion 306 defining each wire 302. In this way, the each outer cylindrical portion 304 covers each respective inner cylindrical portion 306.

In some examples, the outer cylindrical portion 304 includes an NPR foam material, such as a polymer, ceramic, or metal NPR foam material (e.g., a nickel-titanium alloy). In some cases, the NPR foam material is made of a Ti6Al4V alloy that has been transformed from a material exhibiting PPR behavior to a material exhibiting NPR behavior.

The auxetic stent 300 exhibits an overall auxetic behavior in response to a deformation of the auxetic stent 300. Like the auxetic stent 102, the auxetic stent 300 exhibits the overall auxetic behavior even when a PPR material is used in the auxetic stent 300. The overall auxetic behavior of the stent 300 is caused by the geometric pattern of the one or more wires 302. For example, when the one or more wires 302 are arranged in a geometric pattern of re-entrant honeycombs as shown in FIG. 3C, the auxetic behavior can be invoked via heating/cooling of the stent (e.g., in scenarios where the PPR and/or NPR materials include a shape memory property). In this way, the overall auxetic behavior of auxetic stent 300 can be invoked even if the underlying materials themselves (e.g., the material of portions 304 and 306) are not auxetic.

For example, while the outer cylindrical portion 304 includes an NPR foam material in the auxetic stent 300, this is not a requirement to obtain an overall auxetic behavior of auxetic stent 300. Other auxetic stents can include outer cylindrical portions that include a PPR foam and the overall behavior of auxetic can still be auxetic. Furthermore, some auxetic stents that include at least one NPR material can have an overall behavior that is not auxetic. Generally, using at least one NPR material in the auxetic stent 300 enables the stent 300 to take advantage of NPR material properties (e.g., auxetic behavior, increasing surface area as a function of applied deformation, flexibility of the auxetic stent 300 due to the low elasticity of NPR materials, etc.).

In some examples, the porous foam material includes one or more pores 308 disposed on an outer surface of the outer cylindrical portion 304. While FIG. 3B illustrates the one or more pores 308 being located in a cross-section of the wire 302, the one or more pores 308 also exist on the outside diameter of the outer cylindrical portion 304 (e.g., similar to the one or more pores 122 shown in FIG. 1B). This allows the one or more pores 308 to be in contact with vessel 112 of the patient 110.

The outer cylindrical portion 304 is configured to apply a pressure to an inner surface of the vessel 112 of the patient 110 when the auxetic stent 300 is implanted into the vessel 112. The applied pressure facilitates a growth of tissue from the inner surface of the vessel 112 into the one or more pores 308 when the auxetic stent 300 is implanted into the vessel 112.

In some examples, each wire 302 is formed of a material having a shape memory property. For example, the shape memory property can cause the auxetic stent 300 to radially expand when exposed to a temperature of the vessel 112. Additionally, the shape memory property can cause the auxetic stent 300 to radially contract when cooled prior to being implanted into the vessel 112 (e.g., external to the patient 110 prior to surgery).

In some examples, each wire 302 includes a coating of a ceramic material (e.g., hydroxyapatite). For example, the outer cylindrical portion 304 can be coated with hydroxyapatite for improved biocompatibility as compared to an uncoated wire.

Figure 4A:
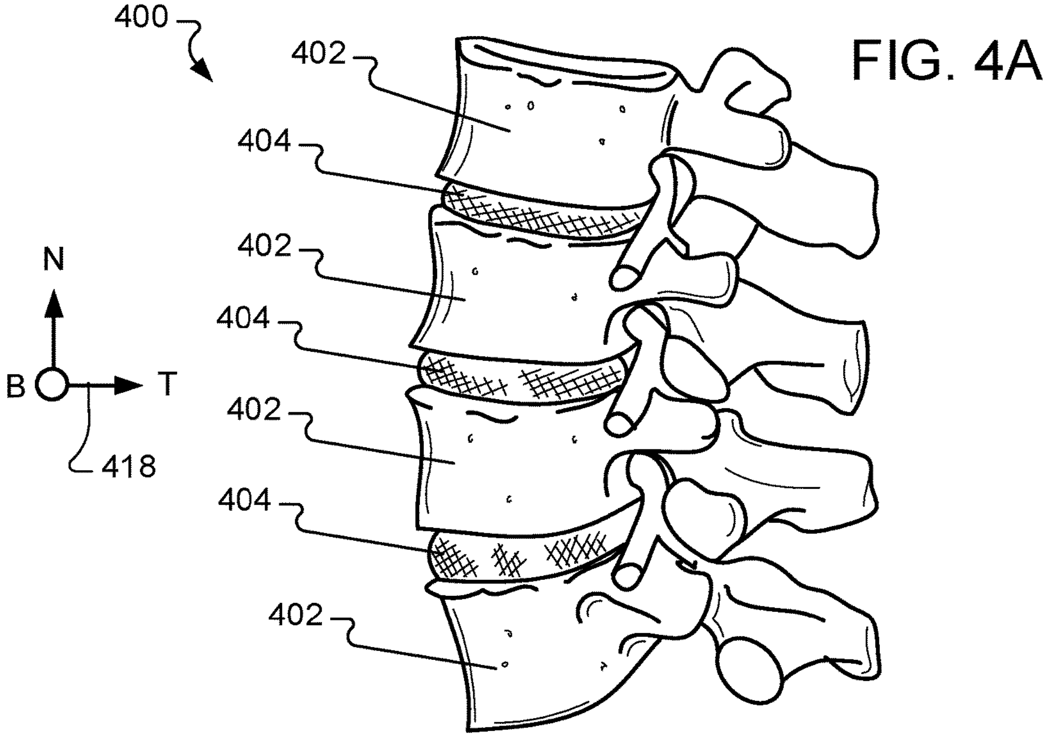
FIG. 4A is an illustration of an auxetic spine disc for use in a vertebrae of a patient.

FIG. 4A is an illustration of an auxetic spine disc 404 (sometimes referred to as a spine disc prosthesis) for use in a vertebrae 400 of a patient (e.g., the patient 110 shown in FIG. 1A). As used herein, an "auxetic spine disc" means that at least a portion of the spine disc exhibits an auxetic behavior when subject to a deformation (e.g., mechanical, thermal, etc.).

The vertebrae 400 includes a plurality of vertebral bodies 402 and intervertebral discs 404. As used herein, "spine discs" refer to intervertebral discs. In general, spine discs are used to provide structural stability to the vertebrae 400 so a patient can stand, walk, etc. An auxetic spine disc 404 can be relevant for a patient undergoing disk replacement surgery, in which a surgeon (not shown) removes a spine disc (e.g., a diseased or poorly positioned spine disc) and replaces the removed spine disc with a replacement spine disc, such as the auxetic spine disc 404.

While FIG. 4A illustrates three auxetic spine discs 404 used in the vertebrae 400, some disc replacement surgery can replace more or fewer spine discs, e.g., one or two, or more than three (e.g., 4, 5, 6, etc.). The number of auxetic spine disc 404 generally depends on a severity of the damage to the patient's vertebrae 400.

Figure 4B:
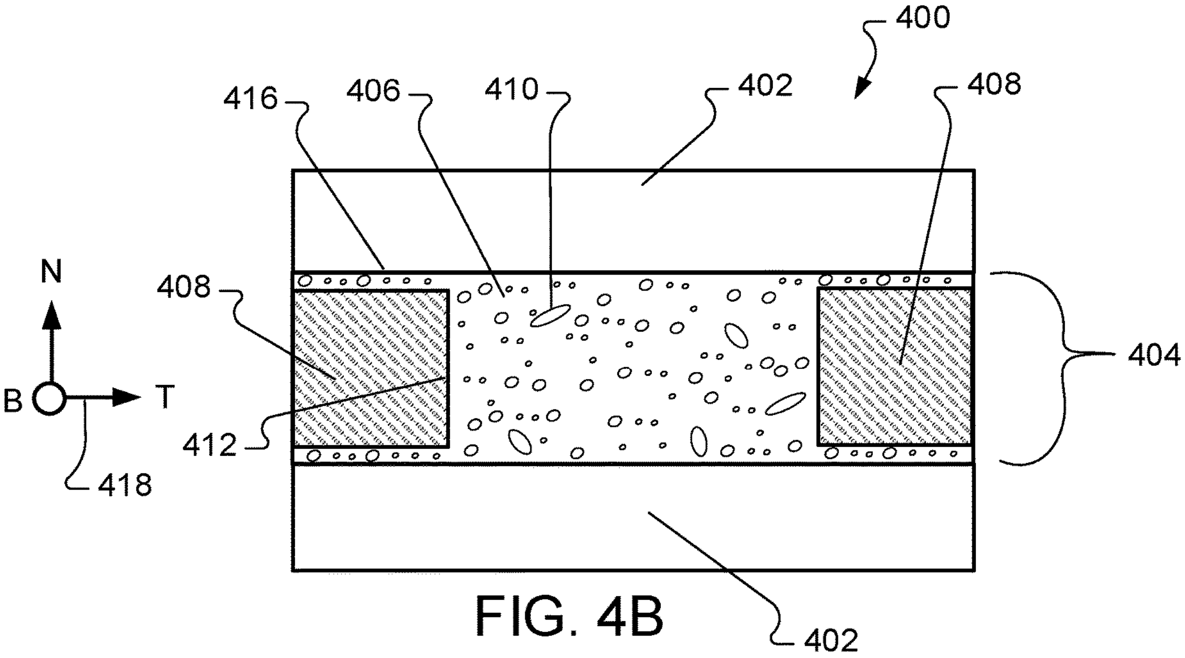
FIG. 4B is a cross-sectional view of the auxetic spine disc of FIG. 4A.
Figure 4C:
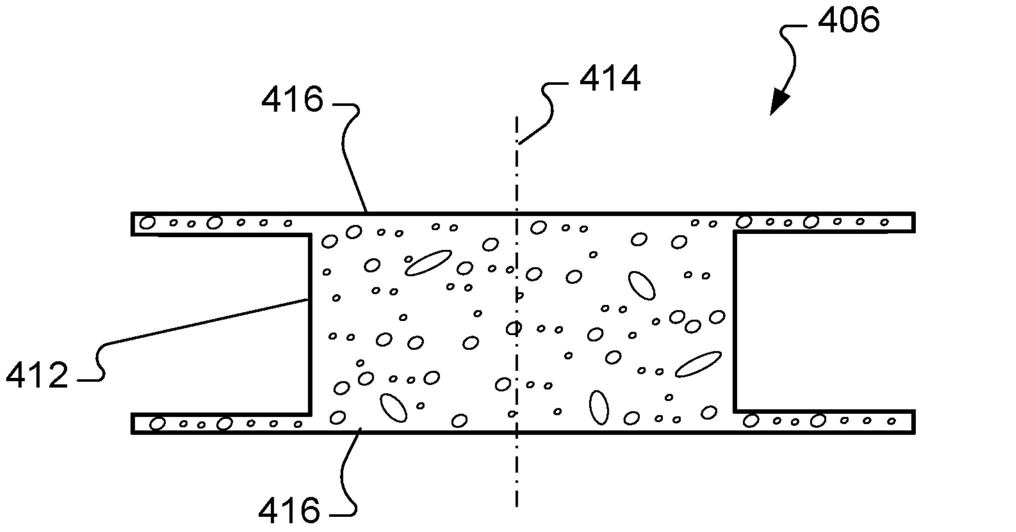
FIG. 4C is a cross-sectional view of a portion of the auxetic spine disc of FIG. 4A.

FIG. 4B is a cross-sectional view of the auxetic spine disc 404 disposed between two adjacent vertebral bodies 402 and FIG. 4C is a cross-sectional view of the first portion 406 of the auxetic spine disc 404. The first portion 406 includes an NPR foam material. In some cases, the NPR foam material is the same as the NPR foam materials described above with reference to the auxetic stents. In an example, the NPR foam material is a titanium alloy, such as a Ti6Al4V alloy. The NPR foam material includes one or more pores 410 disposed on one or more outer surfaces 416 of the first portion 406. In some examples, the NPR foam material is made of a Ti6Al4V foam that has been transformed from a material exhibiting non-auxetic behavior to a material exhibiting auxetic behavior.

Referring to FIG. 4C, the first portion 406 of the spine disc 404 defines a recess 412 extending around an entirety of a perimeter of the first portion 406. In this example, the first portion 406 is axisymmetric about a central axis 414 (e.g., the first portion 406 is circular-shaped) and the recess 412 extends circumferentially around an entire circumference of the first portion 406. In this example, the outer surfaces 416 are perpendicular to the central axis 414.

While the auxetic spine disc 404 includes a circular first portion 406, other auxetic spine discs use differently shaped portions (e.g., non-circular or "D"-shaped, semicircle-shaped, elliptical-shaped, etc.).

Referring again to FIG. 4B, the auxetic spine disc 404 includes a second portion 408 disposed within the recess 412 of the first portion 406. In this way, the first portion 406 is also disposed radially within the second portion 408.

In some examples, the second portion 408 of the spine disc 404 includes a PPR material that is stiffer than the NPR material of the first portion 406. In some examples, the PPR material is the same as any of the PPR materials described above with reference to the auxetic stents. For example, the PPR material can include a metal alloy (e.g., stainless steel or a titanium alloy such as Nitinol.

Like the auxetic stents described above, an overall behavior of the auxetic spine disc 404 can be auxetic even when one or more PPR materials are used. In this example, the overall behavior of the auxetic spine disc 404 is auxetic even when the first portion 406 includes an NPR material and the second portion includes a PPR material. In some cases, the overall auxetic behavior is induced by a deformation of the auxetic spine disc 404.

In some examples, the auxetic spine disc 404 is stiffer in a normal direction N than in a transverse direction T. The normal direction N and transverse direction T are defined using an orthonormal coordinate system 418 where direction N is aligned with the general axis of the vertebrae 400 and direction T is transverse (perpendicular) to the N direction. Direction B is oriented perpendicular to both directions N and T (and, in the example shown, is oriented out of the page of the Figures). Generally, the coordinate system 418 is a local coordinate system defined for each auxetic disc 404 and will has varying directions to account for the local curvature of the vertebrae 400 at the specific location of the auxetic disc 404.

Deformations of the auxetic spine disc 404 can be described with reference to the directions of the orthonormal coordinate system 418. For example, the auxetic spine disc 404 experiences a transverse shear when the first vertebrae body 402 and the second vertebrae body 402 each independently slides in the transverse direction T with respect to each other. The auxetic spine disc 404 experiences a compressive normal force when the first vertebrae body 402 and the second vertebrae body 402 slide in the normal direction N in a contracting motion with respect to each other. The auxetic spine disc 404 experiences a tensile normal force when the first vertebrae body 402 and the second vertebrae body 402 slide in the normal direction N in an expanding motion with respect to each other.

Figure 4D:
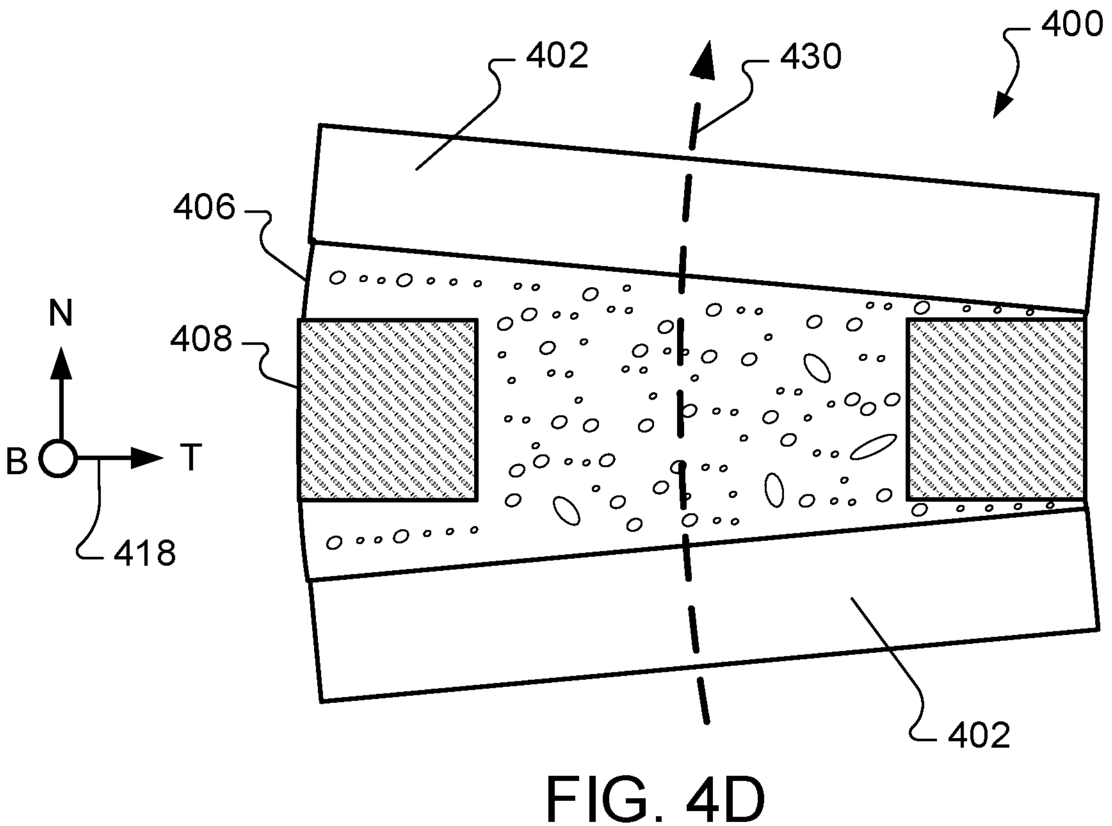
FIG. 4D is a cross-sectional view of the auxetic spine disc of FIG. 4A undergoing a bending deformation.

Referring to FIG. 4D, the auxetic spine disc 404 experiences a bending moment when the first vertebrae body 402 and the second vertebrae body 402 "bend" 430 (or curve) about the bending direction B. This deformation and bending of the auxetic spine disc 404 is important for providing an overall flexibility to the vertebrae 400. If an auxetic spine disc 404 is used that is too stiff in bending or any of the deformations described above, this increased stiffness could cause adjacent spine discs to loosen and create medical problems for the patient. This can happen whether the spine discs are prosthetic or not. For example, the auxetic spine discs described herein are not so stiff that they create such medical problems for patients.

In some examples, the first portion 406 is configured to apply a pressure to a first vertebrae body 402 and an opposing pressure to a second vertebrae body 402 when the auxetic spine disc 404 is implanted between the first vertebrae body 402 and the second vertebrae body 402. The applied pressure can facilitate a growth of tissue from the first vertebrae body 402 and the second vertebrae body 402 into the one or more pores 410 when the auxetic spine disc 404 is implanted between the first vertebrae body 402 and the second vertebrae body 402.

In some examples, at least one of the first portion 406 and the second portion 408 include a material having a shape memory property (e.g., Nitinol). For example, the shape memory property can cause the auxetic spine disc 404 to expand when exposed to a temperature of a body.

In some examples, the auxetic spine disc 404 includes a coating of a ceramic material (e.g., hydroxyapatite). For example, the outer surfaces 416 of the first portion 406 can be coated with hydroxyapatite for improved biocompatibility compared to an uncoated disc.

Figure 5A:
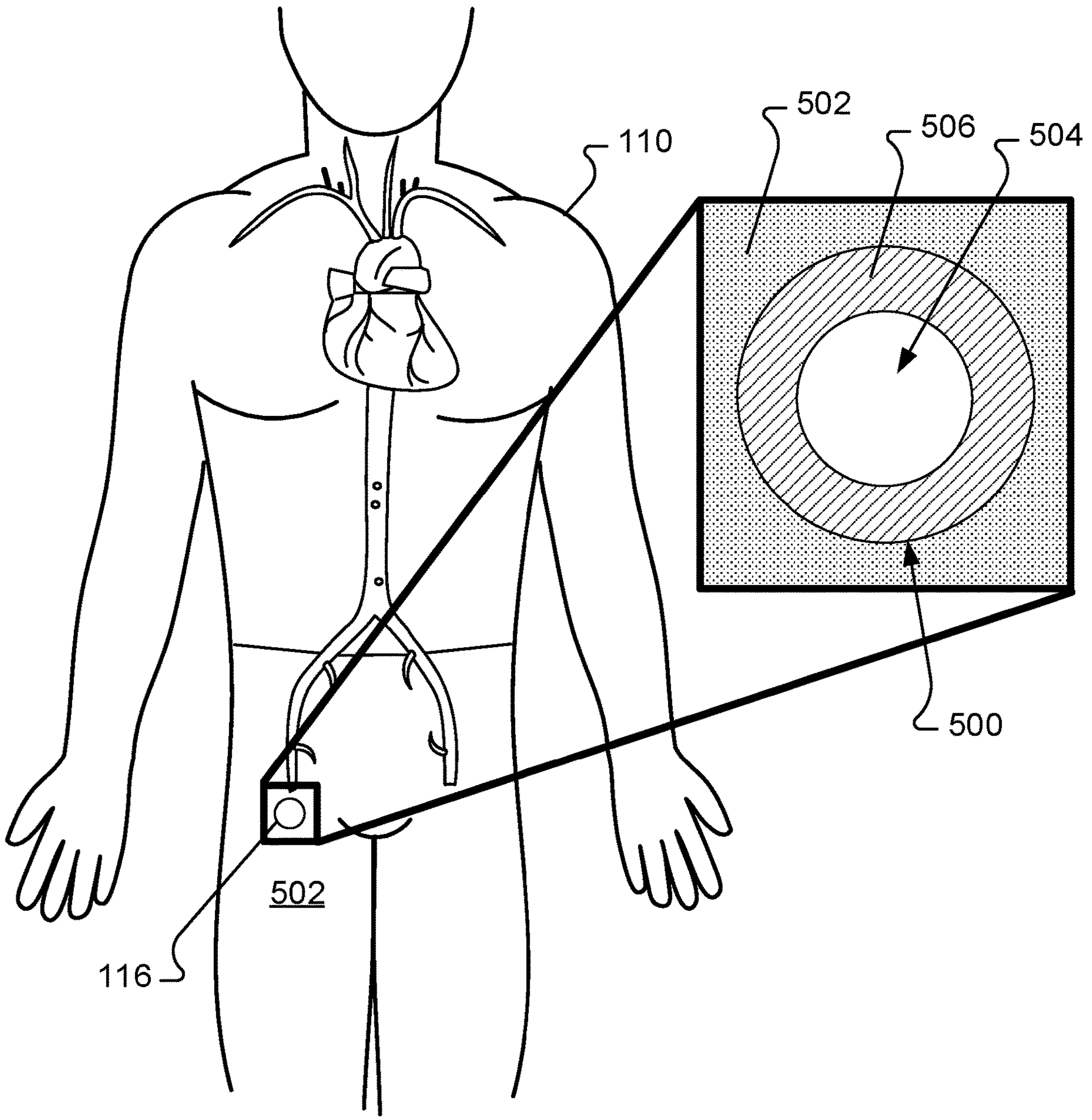
FIG. 5A is an illustration of an auxetic percutaneous device implanted into a patient.

FIG. 5A is an illustration of an auxetic percutaneous device 500 implanted into a patient (e.g., the patient 110). As used herein, an "auxetic percutaneous device" means that at least a portion of the percutaneous device exhibits an auxetic behavior when subject to a deformation (e.g., mechanical, thermal, etc.).

In this example, a surgeon (not shown) cuts an incision 116 into the skin 502 of the patient 110. As described with reference to the auxetic stents above, the incision 116 can be used by the surgeon to pass the a stent (e.g., the auxetic stent 102 or 300) into the artery of the patient 110 and navigate the stent to the implantation site. In addition, an auxetic percutaneous device 500 can be implanted into the patient 110 at the incision location 116 such that surgical tools and/or fluids can be passed through a lumen 504 of the auxetic percutaneous device 500. In some examples, the surgeon passes the stent through the auxetic percutaneous device 500 after the auxetic percutaneous device 500 is implanted in the patient 110.

As shown in FIG. 5A, the auxetic percutaneous device 500 includes a cylindrical portion 506. While the cylindrical portion 506 is cylindrical, other auxetic percutaneous devices can have cross-sections of different shapes (e.g., non-circular such as square, elliptical, "D"-shaped, semicircular, etc.).

Figure 5B:
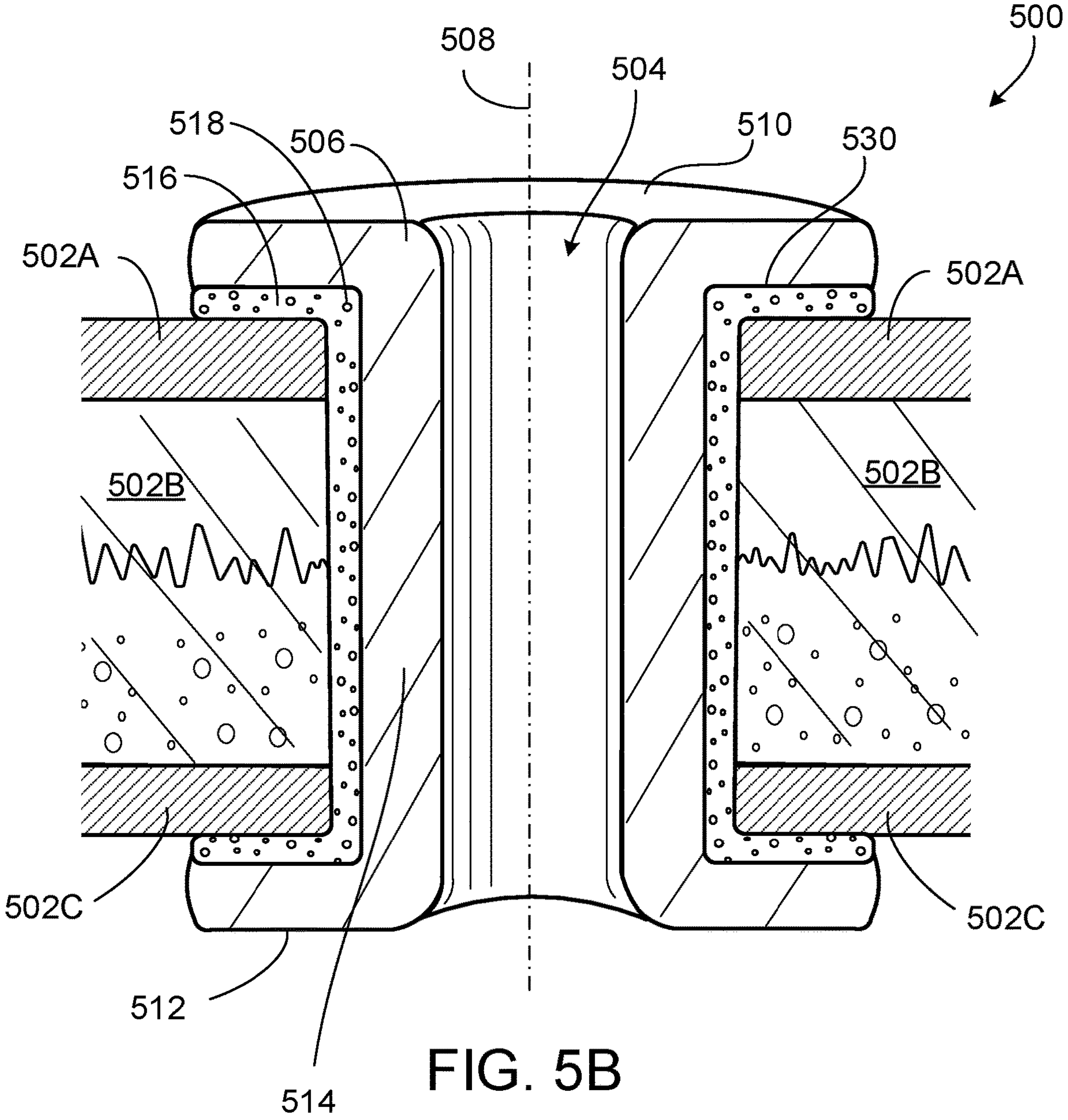
FIG. 5B is a cross-sectional view of the auxetic percutaneous device of FIG. 5A when implanted into the patient.

FIG. 5B is a cross-sectional view of the auxetic percutaneous device 500 when implanted into the patient 110. The cylindrical portion 506 defines a lumen 504 extending through the cylindrical portion 506 along a longitudinal axis 508 of the auxetic percutaneous device 500. As noted above, this lumen 504 can be used to pass fluids, tools, or devices into (or out of) the patient 110.

In some examples, the cylindrical portion 506 includes a PPR material. For example, any of the PPR materials described herein can be used in the cylindrical portion 506. In some examples, the PPR material is a metal alloy such as Nitinol or stainless steel.

The auxetic percutaneous device 500 includes a first end 510 along the longitudinal axis 508 and a second end 512 located opposite the first end. The second end 512 has a larger diameter than the first end 510. The cylindrical portion 506 includes a cylindrical portion 514 between the first end 510 and the second end 512. In general, the diameter of the first end 510 and the second end 512 is patient-dependent. For example, some patients will require a larger auxetic percutaneous device than other patients.

The cylindrical portion 506 defines a cylindrical recess 530 extending radially inward from an outer diameter of the cylindrical portion 506. The cylindrical recess 530 extends around an entire perimeter of the cylindrical portion 506.

The auxetic percutaneous device 500 includes a foam layer 516 disposed within the cylindrical recess 530. In some examples, the foam layer 516 spans circumferentially around an entire circumference of the cylindrical portion 506. In particular, the foam layer 516 is disposed along a path spanning at least three sides of the cylindrical recess 530. In some examples, the foam layer 516 is disposed along each face of the cylindrical recess 530. In some examples, the foam layer 516 covers each face of the cylindrical recess 530.

In some examples, the foam layer includes an NPR foam material. For example, any of the NPR foam materials described herein can be used in the foam layer. For example, the foam layer can be made of a Ti6Al4V alloy that has been transformed from a material exhibiting non-auxetic behavior to a material exhibiting auxetic behavior.

The foam layer 516 includes one or more pores 518 disposed on an outer surface of the foam layer 516. As described above, the one or more pores 518 can be of various shapes (e.g., circular, elliptical, etc.) and have various depths into the foam layer 516.

Like the auxetic stents 102, 300, and the auxetic spine discs 404, the auxetic percutaneous device 500 can exhibit an overall auxetic behavior in response to a deformation of the auxetic percutaneous device 500 even with one or more PPR materials are used in the auxetic percutaneous device 500. For example, even though the cylindrical portion 506 includes a PPR material, because the foam layer 516 includes an NPR material, the overall behavior of the auxetic percutaneous device 500 can be auxetic. However, some auxetic spine discs can have an overall behavior that is non-auxetic. The non-auxetic spine discs can include PPR materials, NPR materials, or a combination thereof.

The foam layer 516 is configured to apply a pressure to one or more layers 502A-502C of a skin 502 of the patient 110 when the auxetic percutaneous device 500 is implanted into the body of the patient 110. In this example, three layers 502A-502C of the skin 502 are illustrated which generally represent an epidermis layer, a dermis layer, and a subcutaneous layer. Additional layers of the skin 502 are not explicitly shown for illustrative convenience.

As shown in FIG. 5B, the skin 502 does not contact the cylindrical portion 506 when the auxetic percutaneous device 500 is implanted into the skin 502. Instead, the skin 502 only contacts the foam layer 516 when the auxetic percutaneous device 500 is implanted into the skin 502. In this way, the skin 502 can include at least two layers of skin 502 and each layer of skin 502 contacts the foam layer 516 when the auxetic percutaneous device 500 is implanted into the skin 502.

The applied pressure facilitates a growth of tissue from the one or more layers 502A-502C of the skin 502 into the one or more pores 518 when the auxetic percutaneous device 500 is implanted into the body of the patient 110 and the deformation is removed. For example, the deformation can be caused by a compression along the longitudinal axis 508. The deformation is removed when the compression is no longer applied. The deformation can also be applied using a temperature difference as described below with reference to a shape memory property.

In some examples, at least one of the cylindrical portion 506 or the foam layer 516 include a material having a shape memory property. In some examples, at least one of the PPR material and the NPR material include a material having a shape memory property.

For example, the shape memory property can induce the cause the deformation of the auxetic percutaneous device 500. In this way, the deformation is removed when the auxetic percutaneous device 500 is allowed to expand when exposed to a temperature of the body. This means that the auxetic percutaneous device 500 changes from a second deformed state (at the cooled condition) back to a first deformation state (at an ambient condition).

In some examples, the auxetic percutaneous device 500 includes a coating of a ceramic material (e.g., hydroxyapatite). For example, the outer surface of the foam layer 516 includes a coating of hydroxyapatite for improved biocompatibility with the patient 110 as compared to an uncoated device.

While the auxetic percutaneous device 500 is described above as being located at an incision site 116, the auxetic percutaneous device 500 can also be implanted into a patient at other locations. For example, the auxetic percutaneous device 500 can be implanted into tissues of organs (e.g., kidney, liver, heart, pancreas, lung, etc.) of the patient 110.

Figure 6A:
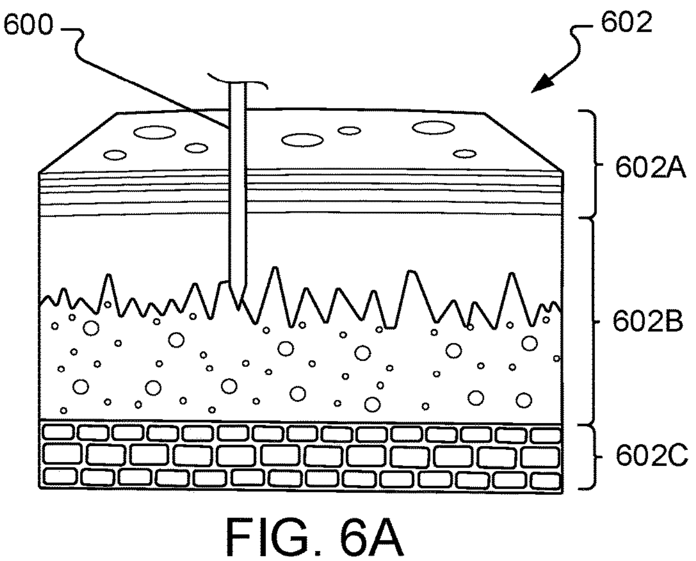
FIG. 6A is an illustration of an auxetic needle penetrating one or more layers of a tissue of a patient.

FIG. 6A is an illustration of an auxetic needle 600 penetrating one or more layers 602A-602C of a tissue 602 of a patient (e.g., the patient 110). As used herein, an "auxetic needle" means that at least a portion of the needle exhibits an auxetic behavior when subject to a deformation (e.g., mechanical, thermal, etc.).

In this scenario, the tissue 602 can be either tissue 602 of an organ of the patient 110 or tissue 602 of a skin of the patient 110. In this example, the auxetic needle 600 is an acupuncture needle used in association with electrotherapy. Details about the acupuncture system are described with reference to FIG. 7 below.

Figure 6B:
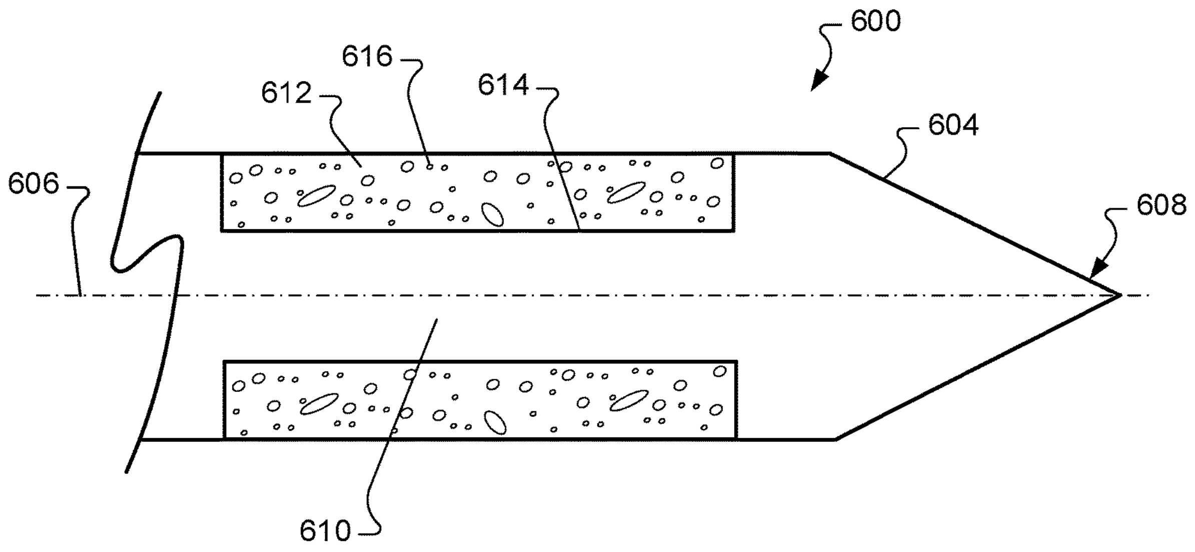
FIG. 6B is a cross-sectional view of the auxetic needle of FIG. 6A.

FIG. 6B is a cross-sectional view of the auxetic needle 600. The auxetic needle 600 includes a cylindrical body 604. In some examples, the cylindrical body 604 includes a PPR material. In some examples, the PPR material is a steel alloy material (e.g., a stainless steel).

The cylindrical body 604 includes a first end 608 along a longitudinal axis 606, a second end along the longitudinal axis 606, and a cylindrical portion 610 between the first end 608 and the second end. The first end 608 defines a tapered tip region configured to penetrate the one or more layers 602A-602C of a tissue 602 of the patient 110.

The cylindrical body 604 is electrically connectable to a piezoelectric energy source for providing electrical energy to the cylindrical body 604 for providing electrotherapy treatment to the one or more layers 602A-602C of the tissue 602 (e.g., depending on an insertion depth of the auxetic needle 600). In some examples, the second end is electrically connectable to the piezoelectric energy source. For example, a wire can connect the second end to the piezoelectric energy source. Further details about the electroacupuncture system are described with reference to FIG. 7 below.

The auxetic needle 600 includes a foam portion 612, e.g., a metal foam, disposed within a circumferential recess 614 of the cylindrical body 604 around the longitudinal axis 606. The circumferential recess 614 spans along the cylindrical portion 610 of the cylindrical body 604. The foam portion 612 includes one or more pores 616.

In some examples, the foam portion 612 includes an NPR material. For example, any of the NPR materials described herein can be used in the auxetic needle 600. In some examples, the foam portion 612 can be made of a Ti6Al4V alloy that has been transformed from a material exhibiting non-auxetic behavior to a material exhibiting auxetic behavior. In other examples, a non-metal foam portion 612 can be used.

The use of an NPR material in the foam portion 612 can increase a surface area of the auxetic needle 600 during a contact with the tissue 602 of the patient. For example, the increased surface area can be formed as a result of the process of transforming a PPR material into an NPR material as described with reference to FIG. 8 below. In some examples, this increased surface area results in a more flexible needle and improves the contact area between the auxetic needle 600 and the tissue 602.

In some examples, electrical energy is transmitted through the cylindrical body 604, through the metal foam portion 612 and into the tissue 602 of the patient. The increased surface area of the foam portion 612 when an NPR material is used increases the electrical contact area between the auxetic needle 600 and the tissue 602 to more effectively transfer the stimulating electric energy to the tissue 602.

In some examples, at least one of the cylindrical body 604 and the foam portion 612 include a material having a shape memory property. For example, the shape memory property can cause the auxetic needle 600 to expand when exposed to a temperature of the body.

In some examples, the auxetic acupuncture needle 600 includes a coating of a ceramic material (e.g., hydroxyapatite).

Figure 7:
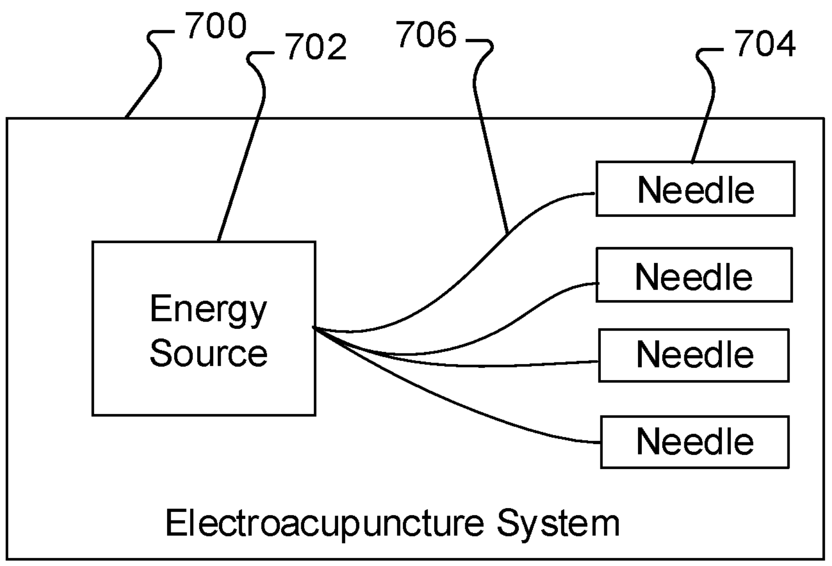
FIG. 7 is a schematic of an electroacupuncture system that uses auxetic needles.

FIG. 7 is a schematic of an electroacupuncture system 700 that uses a plurality of auxetic needles. The electroacupuncture system 700 includes a piezoelectric energy source 702 and a plurality of auxetic acupuncture needles 704. Each auxetic acupuncture needle 704 of the plurality of auxetic acupuncture needles 704 is the same as the auxetic needle 600 described above with reference to FIGS. 6A-6B.

The piezoelectric energy source 702 provides electrical energy to each auxetic acupuncture needle 704 via electrical wires 706 for providing electrotherapy treatment (e.g., to the one or more layers of the skin of the patient 110). In some examples, the piezoelectric energy source 702 includes at least one of quartz (SiO2) or barium titanate (BaTiO3).

In some examples, the electroacupuncture system 700 is used for transferring electrical energy to one or more tissues of a patient. In some cases, the piezoelectric energy source 702 generates electric energy. In some examples, one or more wires 706 transfer the generated electrical energy from the piezoelectric energy source 702 to the cylindrical body 604 of the auxetic acupuncture needle 600. For example, the cylindrical body 604 can include a PPR material and the metal foam portion 612 can include an NPR material, as described above with reference to FIGS. 6A-6B. In some examples, a direct mechanical contact is formed between the cylindrical body 604 and the metal foam portion 612, as describe above with reference to FIGS. 6A-6B.

In some examples, the generated electrical energy is transferred from the cylindrical body 604 to the metal foam portion 612 via this direct mechanical contact between the cylindrical body 604 and the metal foam portion 612. In some examples, the generated electrical energy is transferred, via a mechanical contact between an outer surface of the metal foam portion 612 and the one or more layers of the skin, from the metal foam portion 612 to the one or more one or more layers of the skin of the patient 110 for carrying out the electrotherapy treatment. In some examples, a majority of entire surface area of the outer surface of the metal foam portion 612 is used to transfer the electrical energy to the patient.

In some examples, a surface area of the outer surface of the metal foam portion 612 is increased when the metal foam portion 612 is produced. For example, when the metal foam is transformed from a PPR material to an NPR material, the outer surface area of the metal foam portion 612 is increased. As noted above, this increased surface area can improve the electrical energy transfer between the auxetic acupuncture needle 600 and the patient and this results in an improved electrotherapy treatment for patients. In some examples, NPR foams are produced by transformation of PPR foams to change the structure of the foam into a structure that exhibits a negative Poisson's ratio. In some examples, NPR foams are produced by transformation of nanostructured or microstructured PPR materials, such as nanospheres, microspheres, nanotubes, microtubes, or other nano- or micro-structured materials, into a foam structure that exhibits a negative Poisson's ratio. The transformation of a PPR foam or a nanostructured or microstructured material into an NPR foam can involve thermal treatment (e.g., heating, cooling, or both), application of pressure, or a combination thereof. In some examples, PPR materials, such as PPR foams or nanostructured or microstructured PPR materials, are transformed into NPR materials by chemical processes, e.g., by using glue. In some examples, NPR materials are fabricated using micromachining or lithographic techniques, e.g., by laser micromachining or lithographic patterning of thin layers of material. In some examples, NPR materials are fabricated by additive manufacturing (e.g., three-dimensional (3D) printing) techniques, such as stereolithography, selective laser sintering, or other appropriate additive manufacturing technique.

In an example, a PPR thermoplastic foam, such as an elastomeric silicone film, can be transformed into an NPR foam by compressing the PPR foam, heating the compressed foam to a temperature above its softening point, and cooling the compressed foam. In an example, a PPR foam composed of a ductile metal can be transformed into an NPR foam by uniaxially compressing the PPR foam until the foam yields, followed by uniaxially compression in other directions.

Figure 8:
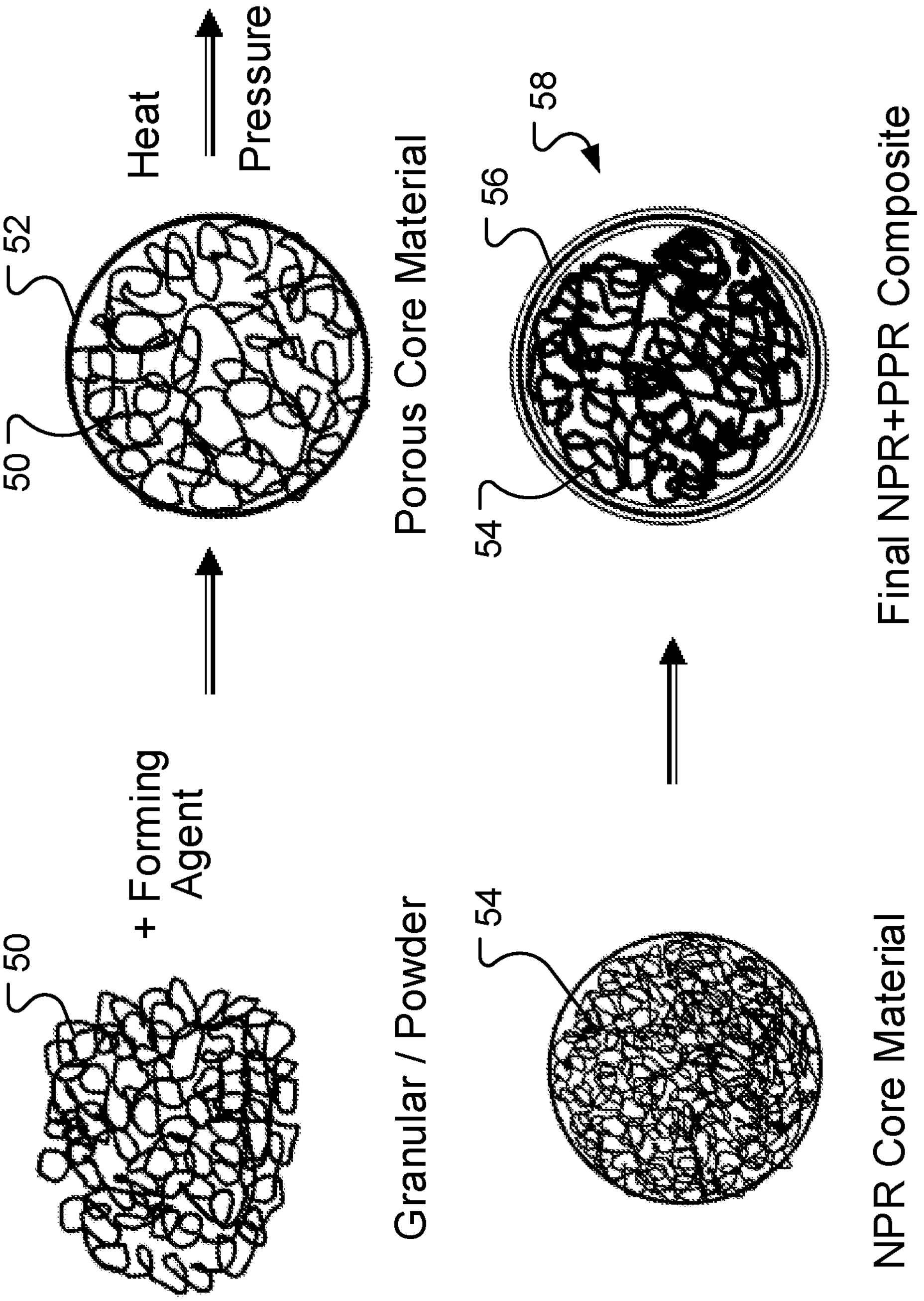
FIG. 8 is a diagram of a process for forming an NPR-PPR composite material.

FIG. 8 is a diagram for forming a medical device with an NPR material. A granular or powdered material, such as a polymer material (e.g., a rubber) is mixed with a foaming agent to form a porous material 50. The porous material 50 is placed into a mold 52. Pressure is applied to compress the material 50 and the compressed material is heated to a temperature above its softening point. The material is then allowed to cool, resulting in an NPR foam 54. In some examples an NPR foam 54 is used with a PPR material.

For example, the medical devices described herein can be composites of PPR and NPR materials. For example, the auxetic stent 102 can include an NPR foam outer cylindrical portion 106 combined with a PPR material inner cylindrical portion 104, the auxetic stent 300 can include an NPR foam outer cylindrical portion 304 combined with a PPR material inner cylindrical portion 306, the auxetic spine disc 404 can include an NPR foam portion 406 combined with a PPR material portion 408, the auxetic percutaneous device 500 can include an NPR foam layer 516 combined with a PPR material portion 506, and the auxetic needle 600 can include an NPR foam portion 612 combined with a PPR material cylindrical portion 610. In these examples, the NPR foam 54 is combined with the PPR material (e.g., generally represented using numeral 56 in FIG. 8) and heat and pressure is applied again to cure the final material into the NPR-PPR composite 58.

Other methods can also be used to fabricate a medical device formed of an NPR material or an NPR-PPR composite material. For example, various additive manufacturing (e.g., 3D printing) techniques, such as stereolithography, selective laser sintering, or other appropriate additive manufacturing technique, can be implemented to fabricate a medical device formed of an NPR material or an NPR-PPR composite. In some examples, different components of the medical device are made by different techniques. For example, the inner portion may be 3D printed while the outer portion is not, or vice versa.

As illustrated by the various example embodiments described herein, auxetic medical devices include, but are not limited to, auxetic stents, auxetic spine discs, auxetic percutaneous devices, and auxetic needles. Furthermore, some of these medical devices can be implanted into a patient. For example, stents, spine discs, and percutaneous devices can be implanted into a patient.

What is claimed is:

1. A stent for insertion into a vessel of a patient, the stent comprising:

an inner tube comprising a positive Poisson's ratio (PPR) material and defining a lumen extending along a longitudinal axis of the stent; and an outer tube comprising a foam material having an anisotropic negative Poisson's ratio (NPR) and disposed around an entirety of the inner tube, the outer tube extending along the longitudinal axis of the stent, wherein the anisotropic NPR foam material of the outer tube defines pores on an outer surface of the outer tube, wherein the pores are re-entrant structures that are polydisperse and randomly arranged;

wherein a hydroxyapatite material is disposed across the anisotropic NPR foam material of the outer tube with the polydisperse and randomly arranged pores that are defined by the re-entrant structures of the anisotropic NPR foam material;

wherein the stent is configured to exhibit an auxetic behavior in response to a deformation of the stent; and wherein at least one of the inner tube or the outer tube is configured to deform from a first deformation state to a second deformation state in response to a transition from a first temperature to a second temperature and to deform from the second deformation state to the first deformation state in response to a transition from the second temperature to the first temperature, where the first temperature is lower than the second temperature.

2. The stent of claim 1, wherein an outer surface of the outer tube is configured to apply a radial pressure to an inner wall of the vessel when the stent is disposed in the vessel and the deformation is removed.

3. The stent of claim 1, wherein the deformation is caused by application of a compressive force along the longitudinal axis of the stent.

4. The stent of claim 1, wherein at least one of the PPR material or the NPR material exhibits a shape memory property.

5. The stent of claim 1, wherein the stent is configured to radially expand from the first deformation state to the second deformation state in response to exposure to the second temperature.

6. The stent of claim 5, wherein the stent is configured to expand along the longitudinal axis in response to the radial expansion.

7. The stent of claim 1, wherein the outer tube covers an entire length of an outer surface of the inner tube such that each axial end of the inner tube is flush with the corresponding axial end of the outer tube in a direction perpendicular to the longitudinal axis of the stent.

8. The stent of claim 1, wherein the PPR material comprises a metal alloy.

9. The stent of claim 1, wherein the NPR foam material comprises a titanium alloy.

10. The stent of claim 9, wherein the titanium alloy comprises a titanium alloy that has been transformed from a non-auxetic titanium alloy to an auxetic titanium alloy.

11. The stent of claim 10, wherein the transformation of the titanium alloy is caused by a combination of compression and heat being applied to the non-auxetic titanium alloy.

12. The stent of claim 1, comprising a coating of a ceramic disposed on an outer surface of the outer tube.

13. The stent of claim 1, wherein the stent is configured to radially contract from the second deformation state to the first deformation state in response to exposure to the first temperature.

14. The stent of claim 13, wherein the stent is configured to contract along the longitudinal axis in response to the radial contraction.

15. The stent of claim 1, wherein the first temperature is ambient temperature and the second temperature is a temperature of the vessel.

16. An implantable medical device for implantation into an anatomical structure, the implantable medical device comprising:

a first cylindrical portion comprising a PPR material; and a second cylindrical portion comprising a foam material having an anisotropic NPR defining pores on an outer surface wherein the pores are re-entrant structures that are polydisperse and randomly arranged, the second cylindrical portion disposed around an entirety of the first cylindrical portion or disposed within the first cylindrical portion;

wherein a hydroxyapatite material is disposed across the NPR foam material of the second cylindrical portion with the polydisperse and randomly arranged pores that are defined by the re-entrant structures of the NPR material;

wherein the implantable medical device is configured to exhibit an auxetic behavior in response to a deformation of the implantable medical device; and wherein at least one of the first cylindrical portion or the second cylindrical portion is configured to deform from a first deformation state to a second deformation state in response to a transition from a first temperature to a second temperature and to deform from the second deformation state to the first deformation state in response to a transition from the second temperature to the first temperature, where the first temperature is lower than the second temperature.

17. The implantable medical device of claim 16, wherein the outer surface of the second cylindrical portion is configured to apply a pressure to an inner surface of the anatomical structure when the implantable medical device is implanted in the anatomical structure and the deformation is removed.

18. The implantable medical device of claim 16, wherein at least one of the PPR material or the NPR foam material exhibits a shape memory property.

19. The implantable medical device of claim 16, wherein the anatomical structure comprises a vessel, an organ or a skin.

20. The implantable medical device of claim 16, wherein the implantable medical device comprises an auxetic stent or an auxetic percutaneous device.

21. The implantable medical device of claim 16, wherein the implantable medical device is configured to radially contract from the second deformation state to the first deformation state in response to exposure to the first temperature.

22. The implantable medical device of claim 21, wherein the implantable medical device is configured to axially contract in response to the radial contraction.

23. The implantable medical device of claim 16, wherein the implantable medical device is configured to radially expand from the first deformation state to the second deformation state in response to exposure to the second temperature.

24. The implantable medical device of claim 23, wherein the implantable medical device is configured to axially expand in response to the radial expansion.

* * * * *